(12) United States Patent  (10) Patent No.: US 8,361,996 B2
Bansal et al.  (45) Date of Patent: Jan. 29, 2013

(54) IMIDAZOLYL SUBSTITUTED STEROIDAL AND INDAN-1-ONE DERIVATIVES

(75) Inventors: Ranju Bansal, Chandigarh (IN); Sheetal Guleria, Chandigarh (IN); Gaurav Narang, Chandigarh (IN); Rolf Wolfgang Hartmann, Saarbrucken (DE)

(73) Assignee: Council of Scientific and Industrial Research, New Delhi (IN)

( * ) Notice: Subject to any disclaimer, the term of this patent is extended or adjusted under 35 U.S.C. 154(b) by 909 days.

(21) Appl. No.: 11/992,141

(22) PCT Filed: Sep. 8, 2006

(86) PCT No.: PCT/IB2006/002471
§ 371 (c)(1),
(2), (4) Date: Aug. 11, 2008

(87) PCT Pub. No.: WO2007/031833
PCT Pub. Date: Mar. 22, 2007

(65) Prior Publication Data
US 2009/0137541 A1  May 28, 2009

(30) Foreign Application Priority Data
Sep. 15, 2005  (IN) .......................... 2498/DEL/2005

(51) Int. Cl.
*A61K 31/58* (2006.01)
*A61K 31/565* (2006.01)
*A61K 31/566* (2006.01)
*C07J 1/00* (2006.01)
*C07J 41/00* (2006.01)
*C07J 43/00* (2006.01)

(52) U.S. Cl. .......... 514/176; 514/177; 514/182; 540/96; 540/108; 552/636; 552/638

(58) Field of Classification Search .................... 540/96, 540/108; 514/176, 177, 182; 552/636, 638
See application file for complete search history.

(56) References Cited

U.S. PATENT DOCUMENTS
5,567,694 A * 10/1996 Almirante et al. ............ 514/169

FOREIGN PATENT DOCUMENTS
WO  WO 96/40150  * 12/1996

OTHER PUBLICATIONS

International Search Report issued by the International Searching Authority (ISA/EPO) on Mar. 23, 2007 in connection with International Application No. PCT/IB2006/002471.

* cited by examiner

*Primary Examiner* — Barbara P Badio
(74) *Attorney, Agent, or Firm* — John P. White; Cooper & Dunham LLP

(57) ABSTRACT

The present invention provides a novel series of imidazolyl substituted steroidal and indan-1-one derivatives and salts thereof having the following general structural formulae (A and B)

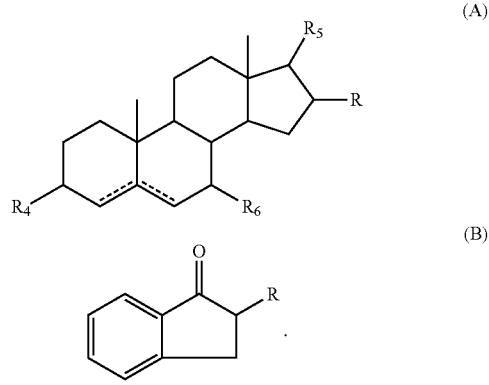

6 Claims, No Drawings

IMIDAZOLYL SUBSTITUTED STEROIDAL AND INDAN-1-ONE DERIVATIVES

This application is a §371 national stage of PCT International Application No. PCT/IB2006/002471, filed Sep. 8, 2006, and claims priority of Indian Patent Application No. 2498/DEL/2005, filed Sep. 15, 2005, the contents of all of which are hereby incorporated by reference into this application.

The present invention relates to Novel series of imidazolyl substituted steroidal and indan-1-one derivatives. The present invention also relates to novel imidazole ring substituted steroidal as non-steroidal aromatase inhibitors. This invention particularly relates to provide the process of preparation of such derivatives and their biological activity as potent aromatase inhibitory compounds.

Aromatase is the physiological enzyme responsible for the conversion of androgens such as androstenedione or testosterone, into estrogens e.g., estrone and estradiol, respectively (Simpson E R et al, Endocrine Reviews, 1994, 15: 342-355). Inhibition of aromatase, a cytochrome P-450 enzyme, has become a strategy of choice to interfere with normal or pathological estrogen-induced or estrogen-dependent biological processes such as female sexual differentiation, ovulation, implantation, breast and endometrial cell proliferation as well as regulation of spermatogenesis or prostate cell proliferation of male or of non-reproductive functions such as bone formation or Immune T cell and cytokine balance (Simpson E R et al., Recent progress in Hormone research, 1997, 52: 185-213) and also in the treatment of disseminated estrogen dependent breast cancer over the last three decades (Tomera J. F., Drugs of Today, 1994, 30, 565-574; Howell A., Dowsett M., BMJ. 1997).

A number of steroidal and non-steroidal compounds affecting estrogen biosynthesis through the inhibition of aromatase are presently in the market and others are in various stages of clinical trials for the treatment of breast cancer. (Njar, V. C. O; Brodie, A. M. H, Drugs, 1999, 58, 233-255; Seralini G E, Moslemi, S. Mol. Cell. Endocrinol, 2001, 178, 117-131).

The steroidal inhibitors are generally more specific, but have the potential to induce unwanted agonist effects. In contrast, non-steroidal inhibitors may lack specificity because they have the potential to block several $P_{450}$ mediated steroidal conversions but are less likely to exhibit unwanted agonist effects of steroids.

Steroidal inhibitors such as 4-hydroxyandrostenedione (formestane) (Carlini, P. et al., Ann. Oncol., 2001, 12, 1539-1543) and atamestane (Traina, T A. et al., Curr. Opin. Invest. Drugs., 2004, 605-610) compete with the endogenous substrates, androstenedione and testosterone, for the active site of the enzyme, where they act as false substrates and are processed to intermediates that bind irreversibly to the active site, causing irreversible enzyme inhibition.

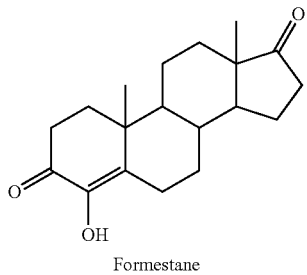

Formestane

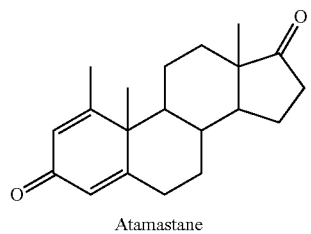

Atamastane

Nonsteroidal inhibitors also compete with the endogenous substrates for access to the active site, where they then form a coordinate bond to the heme iron atom. Therefore, they effectively exclude both the natural substrate) and oxygen from the enzyme.

A large number of azole derivatives are traditionally known as antifungal agents. Some of the imidazole and triazole derivatives have already been described as inhibitors of enzyme aromatase. Generally the imidazolyl and triazole groups are generally associated with aromatic rings as in letrozole (Buzdar A et al., Proc. Am. Soc. Clin. Oncol. 1996; Lamb H M and Adkins J C, Drugs, 1998, 56: 1125-1140) and anastrozole (Wiseman L R and Adkins J C, Drugs Aging, 1998, 13, 321-332) or linked via a methylene group to a benzotriazole are described in EP-A-293-978. Fadrozole, an imidazole derivative, is a potent competitive inhibitor of aromatase both in vitro and in vivo and is more selective than aminoglutethimide.

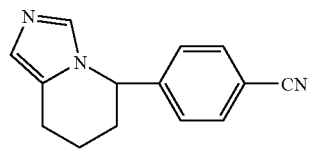

Fadrozole

Hartmann et al (J. Med. Chem., 1994, 37, 1275-1281) had also described some pyridyl substituted indanones and tetralones as potent and selective non-steroidal anti-aromatase agents, when compared with standard drug aminoglutethimide.

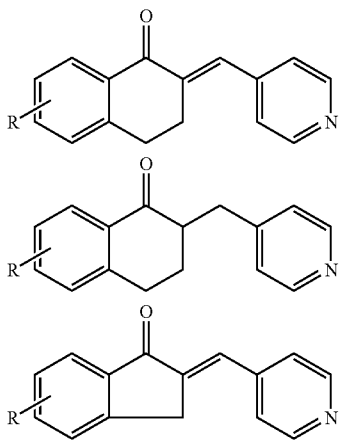

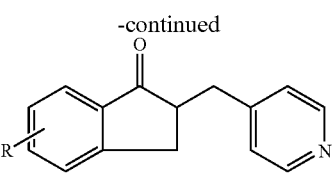

Further, their hydroxy and methoxy derivatives at 5 and 6 positions have also shown 150-200 times more activity as compared to aminoglutethimide.

Accordingly, the main object of this invention is to provide certain new imidazolyl substituted steroidal and indanone derivatives. Another object is to provide a process for preparation of such newer steroidal as well as non-steroidal aromatase inhibitors.

Further object of the invention is to provide the imidazolyl substituted steroidal and indanone derivatives which showed better relative potency as compared to standard drug aminoglutethimide.

Accordingly, the present invention provides a novel series of imidazolyl substituted steroidal and indan-1-one derivatives and salts thereof having the following general structural formulae (A and B)

(A)
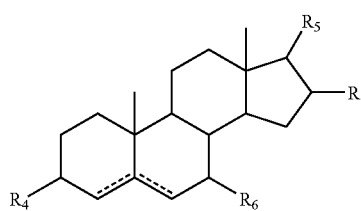

and (B)
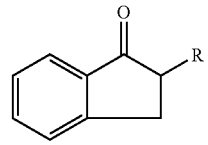

wherein R is

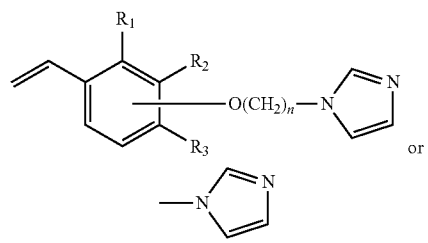

or

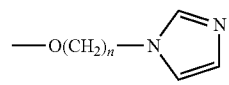

$R_1$, $R_2$ and $R_3$ independently represent H, or —$OCH_3$ or

—$O(CH_2)_n$—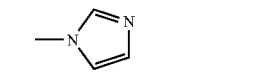

$R_4$ and $R_5$ independently represent —OH, or =O or —$OCOCH_3$ groups $R_6$ independently represents H or

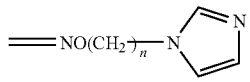

moieties.

$n=2$ or $3$, A double bond is either present between 4 and 5 or 5 and 6 positions of the steroidal nucleus in case of steroidal derivatives.

In an embodiment of the invention a novel series of imidazolyl substituted steroidal derivatives of formula A, wherein the 16-substituted-androst-5-ene steroidal derivatives having general formula:

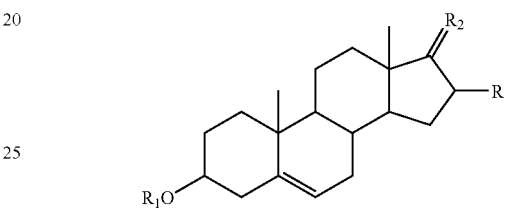

$R_1$ = H, $R_2$ = H and OH
or
$R_1$ = H, $R_2$ = O
or
$R_1$ = Ac, $R_2$ = O
or
$R_1$ = Ac, $R_2$ = H and OAc R =
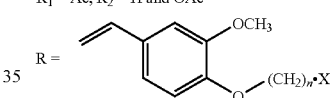

or
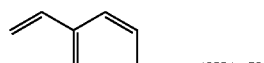

or
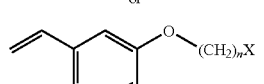

or
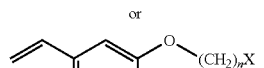

or
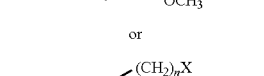

or
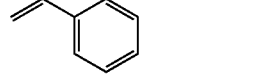

$n = 2, 3$
$X = Cl$ or —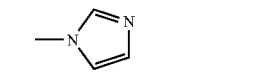

In another embodiment of the invention a novel series of imidazolyl substituted steroidal derivatives of formula A, wherein the 16-substituted-androst-4-ene-3,17-dione is having general formula:

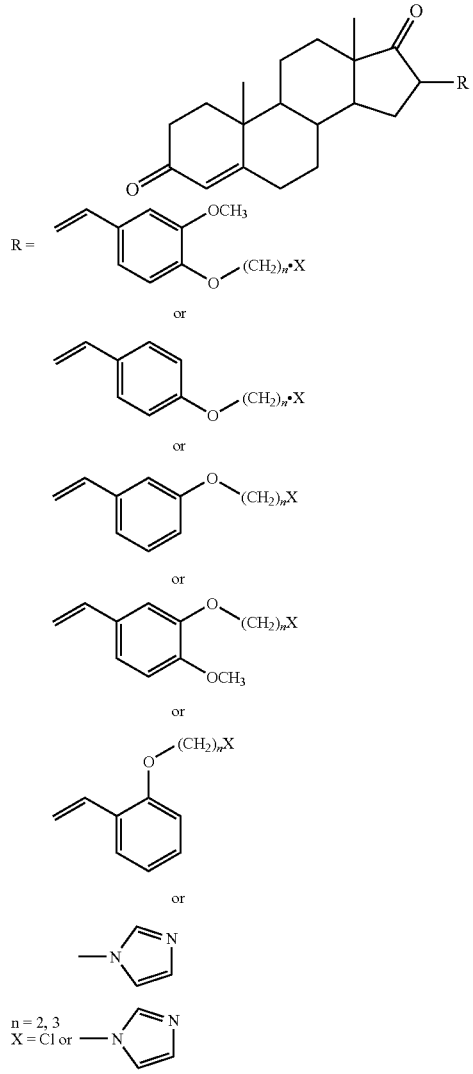

In yet another embodiment of the invention a novel series of imidazolyl substituted steroidal derivatives of formula A, wherein the 7-substituted-androst-5-ene steroidal derivatives having general formula:

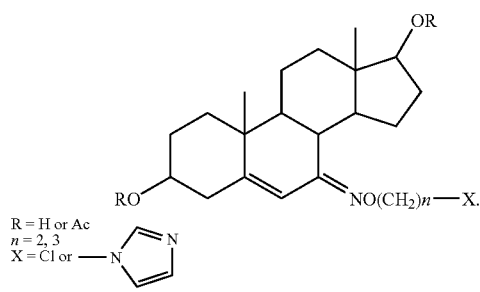

In a further embodiment of the invention a novel series of imidazolyl substituted steroidal derivatives of formula A, wherein the structure of 16-substituted steroidal compound is

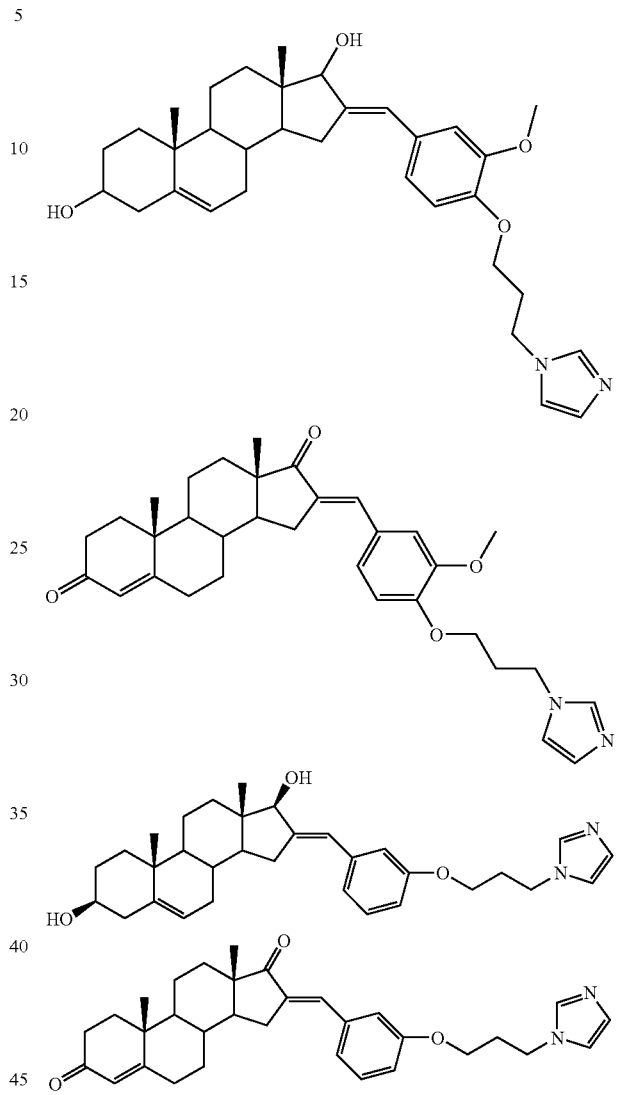

In a further embodiment of the invention a novel series of imidazolyl substituted steroidal derivatives of formula A, wherein the representative compounds of imidazolyl substituted steroidal derivatives are:

16-[4-{3-(Imidazol-1-yl)propoxy}-3-methoxybenzylidene]-17-oxo-5-androst-en-3β-ol (12) (DPJ-RG-1151)

16-[4-{3-(Imidazol-1-yl)propoxy}-3-methoxybenzylidene]-17-oxo-5-androsten-3β-yl acetate (13) (DPJ-RG-1196)

16-[4-{3-(Imidazol-1-yl)propoxy}-3-methoxybenzylidene]-5-androstene-3β,17β-diol (14) (DPJ-RG-1219)

16-[4-{3-(Imidazol-1-yl)propoxy}-3-methoxybenzylidene]-5-androstene-3β,17β-diol diacetate (15) (DPJ-RG-1227)

16-[4-{3-(Imidazol-1-yl)propoxy}-3-methoxybenzylidene]-4-androstene-3,17-dione (16) (DPJ-RG-1177)

16-[3-{3-(imidazol-1-yl)propoxy}benzylidene]-17-oxo-5-andro-sten-3β-ol (18) (DPJ-RG-1307)

16-[3-{3-(imidazol-1-yl)propoxy}benzylidene]-17-oxo-5-andro-sten-3β-yl acetate (19) (DPJ-RG-1309)

16-[3-{3-(imidazol-1-yl)propoxy}benzylidene]-5-androstene-3β,17β-diol (20) (DPJ-RG-1310)

16-[3-{3-(imidazol-1-yl)propoxy}benzylidene]-5-androstene-3β,17β-diol diacetate (21) (DPJ-RG-1311)

16-[3-{3-(imidazol-1-yl)propoxy}benzylidene]-4-androstene-3,17-dione (22) (DPJ-RG-1308)

7-[O-{3-(Imidazol-1-yl)propyl}oximino]-5-androstene-3β,17β-diol (25) (DPJ-RG-1223)

16β-(Imidazol-1-yl)-17-oxo-5-androsten-3β-ol (27) (DPJ-RG-1240)

16β-(Imidazol-1-yl)-5-androstene-3β,17β-diol (28) (DPJ-RG-1317)

16β-(Imidazol-1-yl)-5-androstene-3β,17β-diol diacetate (29) (DPJ-RG-1318)

16β-(Imidazol-1-yl)-4-androstene-3,17-dione (30) (DPJ-RG-1241)

In another embodiment of the invention a novel series of imidazolyl substituted indan-1-one derivatives of formula B, wherein the indan-1-one derivatives have general formula as:

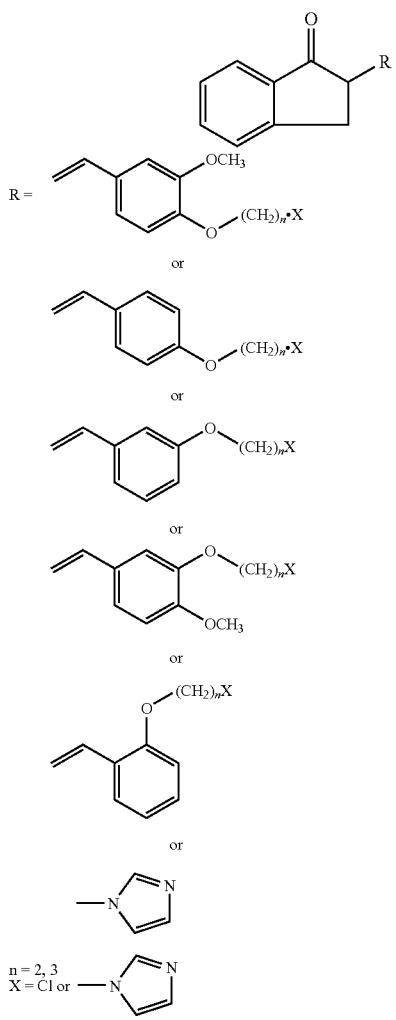

In another embodiment of the invention a novel series of imidazolyl substituted indan-1-one derivatives wherein, representative compounds of indan-1-one derivatives are:

2-[3-(3-Imidazol-1-yl-propoxy)-benzylidene]-indan-1-one (2) (DPJ-RG-1088)

2-[2-(3-Imidazol-1-yl-propoxy)-benzylidene]-indan-1-one (4) (DPJ-1055)

2-[3-(3-Imidazol-1-yl propoxy)-methoxybenzylidene)indan-1-one (6) (DPJ-RG-1090)

2-[4-(3-Imidazol-1-yl propoxy)-3-methoxybenzylidene)indan-1-one (8) (RG-DPJ-195)

2-[3-(2-Imidazol-1-yl ethoxy)-benzylidene]indan-1-one (10) (RG-DPJ-325)

2-(1H-1-imidazolyl)-1-indanone (32)

In another embodiment of the invention a novel series of imidazolyl substituted indan-1-one derivatives wherein the salt may be selected from any pharmaceutically acceptable salt.

In another embodiment of the invention a novel Use of the compounds wherein the compounds having general formula A and B shows aromatase inhibitory activity.

In another embodiment of the invention the novel compounds of the series wherein the $IC_{50}$ values for the aromatase inhibitory activity of the potent compounds 2, 4, 6, 8, 14, 16, 20, 22, 24, 25, 27 and 30 is ranging between 0.18-12 μM with relative potency of these compounds ranging from 2.5 to 165.3 times as compared to standard drug aminoglutethimide.

The novel compounds wherein the compounds are useful as anticancer agents. Accordingly, the present invention provides a process for preparation of 16-substituted-androstene compounds of formula A comprising; base catalysed aldol condensation of DHA with chloroalkylated aldehydes of formula C at room temperature to afford halogenated aldol adducts and followed by thermal fusion of these chloroalkoxybenzylidene derivatives of DHA with imidazole at a temperature ranging between 130-140° C., to afford imidazolyl substituted aldol products, converting the said aldol products obtained into corresponding 5-androstene-3,17-diacetate compounds or oxidizing to 4-androstene-2,17-dione compounds or to 5-androstene-3-aceoxy-17-one or to 5-androstene-3,17-diol compounds by known methods.

In another embodiment of the invention a novel process wherein 3-acetoxy-17-one-5-androstene steroid is prepared from 3-hydroxy precursor by treatment with acetic anhydride and dry pyridine in steam bath for about 2 hrs.

In another embodiment of the invention a novel process wherein androst-5-en-3,1-diol was formed by sodium borohydride reduction of 3-hydroxy-17-one-5-androstene steroid at room temperature which on treatment with acetic anhydride and pyridine in steam bath for about 2 hrs gave 3,17-diacetoxy-5-androstene aldol products.

In another embodiment of the invention a novel process wherein the preparation of 4-androstene-3,17-dione steroidal aldol products were prepared by Oppenauer oxidation of 5-androstene-3-hydroxy-17-one aldol products. Accordingly the present invention provides a novel process for the preparation of 7-substituted-5-androstene steroidal derivatives possessing Imidazole ring of formula A, comprising: treating 7-hydroximino-5-androstene derivative, prepared by known methods, with 1-bromo-3-chloropropane and subsequent thermal fusion with imidazole and followed by its hydrolysis.

In an embodiment of the invention a novel process for the preparation of 16-Imidazolylandrostene steroids comprising; brominating DHA by refluxing with cupric bromide in methanol and benzene to give 16-bromo derivatives and their subsequent thermal fusion with powdered imidazole at a temperature ranging between 130-140° C.

Accordingly the present invention provides a Process for preparation of 2-aminoalkoxybenzylidene-1-indanone of formula B, comprising; base catalysed aldol condensation of 1-indanone with chloroalkylated aldehydes of formula C at room temperature to afford halogenated aldol adducts followed by thermal fusion of chloroalkoxybenzylidene derivatives of 1-indanone with imidazole at a temperature ranging between 80-90° C., to afford imidazolyl substituted aldol products of formula B.

In an embodiment of the invention a process for the preparation of 2-imidazolyl-1-indanone wherein the said compound is prepared by thermal fusion of 2-bromo-1-indanone with powdered imidazole at a temperature ranging between 80-90° C.

In the embodiment of the present invention, the aromatase inhibitory activity of these compounds is monitored by measuring the $^3H_2O$ formed from [1β,2β-$^3$H] testosterone during aromatization. These compounds produced a concentration dependent inhibition of aromatase, which in many cases is significantly higher than that of standard drug aminoglutethimide.

DETAILED DESCRIPTION

The compounds which comprise in the present invention have the following general structural formulae (A and B)

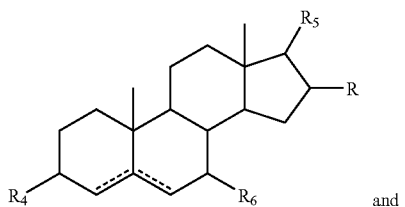

(A)

and

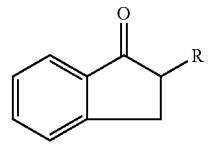

(B)

Wherein R independently represents

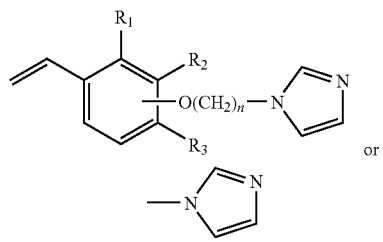

or

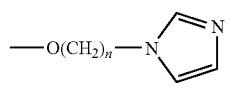

$R_1$, $R_2$ and $R_3$ independently represent H, or —$OCH_3$ or

—O(CH$_2$)$_n$—N⟨imidazole⟩

$R_4$ and $R_5$ independently represent —OH, or =O or —OCOCH$_3$ groups $R_6$ independently represents H or

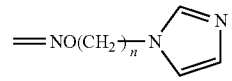

moieties.
n=2 or 3
A double bond is either present between 4 and 5 or 5 and 6 positions of the steroidal nucleus in case of steroid derivatives.

In preferred compounds of the invention, of outstanding interest are: 2-[3-(3-Imidazol-1-yl-propoxy)-benzylidene]-indan-1-one (2) (DPJ-RG-1088); 2-[2-(3-Imidazol-1-yl-propoxy)-benzylidine]-indan-1-one (4) (DPJ-1055); 2-[3-(3-Imidazol-1-yl propoxy)-4-methoxybenzylidene)indan-1-one (6) (DPJ-RG-1090); 2-[4-(3-Imidazol-1-yl propoxy)-3-methoxybenzylidene)indan-1-one (8) (RG-DPJ-195); 2-[3-(2-Imidazol-1-yl ethoxy)-benzylidine]indan-1-one (10) (RG-DPJ-325); 2-(1H-1-imidazolyl)-1-indanone (32); 16-[4-{3-(Imidazol-1-yl)propoxy}-3-methoxy-benzylidene]-17-oxo-5-androsten-3β-ol (12) (DPJ-RG-1151); 16-[4-{3-(Imidazol-1-yl)propoxy}-3-methoxy-benzylidene]-17-oxo-5-androsten-3β-yl acetate (13) (DPJ-RG-1196); 16-[4-{3-(Imidazol-1-yl)propoxy}-3-methoxybenzylidene]-5-androstene-3β,17β-diol (14) (DPJ-RG-1219); 16-[4-{3-(Imidazol-1-yl)propoxy}-3-methoxybenzylidene]-5-androstene-3β,17β-diol diacetate (15) (DPJ-RG-1227); 16-[4-{3-(Imidazol-1-yl)propoxy}3-methoxybenzylidene]-4-androstene-3,1-dione (16) (DPJ-RG-1177); 16-[3-{3-(imidazol-1-yl)propoxy}benzylidene]-17-oxo-5-androsten-3β-ol (18) (DPJ-RG-1307); 16-[3-{3-(imidazol-1-yl)propoxy}benzylidene]-17-oxo-5-andro-sten-3β-yl acetate (19) (DPJ-RG-1309); 16-[3-{3-(imidazol-1-yl)propoxy}benzylidene]-5-androstene-3β,17β-diol (20) (DPJ-RG-1310); 16-[3-{3-(imidazol-1-yl)propoxy}benzylidene]-5-androstene-3β,17β-diol diacetate (21) (DPJ-RG-1311); 16-[3-{3-(imidazol-1-yl)propoxy}benzylidene]-4-androstene-3,17-dione (22) (DPJ-RG-1308); 7-[O-{3-(Imidazol-1-yl)propyl}oximino]-5-androstene-3β,17β-diol (25) (DPJ-RG-1223); 16β-(Imidazol-1-yl)-17-oxo-5-androsten-3β-ol (27) (DPJ-RG-1240); 16β-(Imidazol-1-yl)-5-androstene-3β,17β-diol (28) (DPJ-RG-1317); 16β-(Imidazol-1-yl)-5-androstene-3β,17β-diol diacetate (29) (DPJ-RG-1318); 16β-(Imidazol-1-yl)-4-androstene-3,17-dione (30) (DPJ-RG-1241)

The steroidal as well as non-steroidal compounds of general formulae (A) and (B) (wherein R is

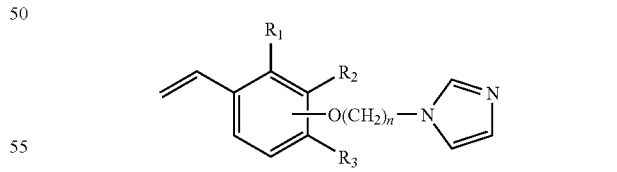

and $R_1$, $R_2$, $R_3$, $R_4$, $R_5$ and $R_6$ are as herein before defined) which comprise the present invention have been prepared by the aldol condensation of some alkylated aldehydes with steroidal or ☐ndanones nucleus. These aldol products were then subjected to fusion with imidazole to get the desired products.

The alkylated aldehydes of general formula © (where $R_1$, $R_2$ and $R_3$ independently represent H or —$OCH_3$ or —O(CH$_2$)$_n$Cl, n=2 or 3) were prepared by treating the corresponding aldehydes; salicylaldehyde, 3-hydroxybenzaldehyde, 4-hydroxybenzaldehyde, isovanillin or vanillin with either 3-bromo-1-chloropropane or 2-bromo-1-chloroethane in the presence of anhydrous potassium carbonate.

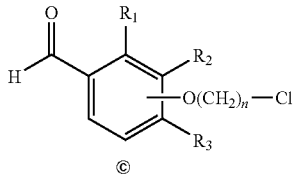

These aldehydes of general formula © were then subjected to aldol condensation [Nielsen, A. T.; Houlihan, W. J. The aldol Condensation. In *Organic Reactions*, 16$^{th}$ ed. (John Wiley: New York) 1968; 1-438] with dehydroepiandrosterone (DHA) or with indan-1-one to give various aldol products, and were subsequently thermally fused with imidazole, which has been described as a pharmacologically active heterocyclic ring with potential for aromatase inhibition in literature [Adje, N. et al 1-N-Phenylamino-1H-imidazole derivatives as aromatase inhibitors and pharmaceutical compositions containing them, (Laboratoire Thermax) U.S. Pat. No. 6,737,433 B1, 2004], to develop new derivatives of interest for aromatase inhibition of general formulae (A) and (B) wherein R is

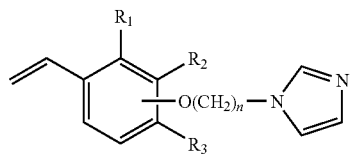

and $R_1$, $R_2$ and $R_3$ are herein as before described and in case of steroidal derivatives, $R_4$=—OH, $R_5$ represents =O, $R_6$=H and a double bond is present between 5 and 6 positions.

According to a feature of present invention, the steroidal derivatives of general formula (A) wherein $R_4$ independently represents —OCOCH$_3$ group and $R_5$ independently represent =O group, $R_6$=H and a double bond is present between 5 and 6 positions were in turn prepared by acetylation of 17-keto-3-hydroxy DHA aldol product with acetic anhydride in dry pyridine.

According to a feature of the present invention the steroidal aldol products of general formula (A) wherein both $R_4$ and $R_5$ independently represents —OH group, were inturn prepared by reducing the 17-keto-3-hydroxy DHA aldol product with sodium borohydride in methanol.

The derivatives of general formula (A) wherein both $R_4$ and $R_5$ independently represent —OCOCH$_3$ group was prepared by direct acetylation of previously described 3,17-dihydroxy aldol products with acetic anhydride in dry pyridine.

According to a feature of present invention, the derivatives of general formula (A) wherein both $R_4$ and $R_5$ represent =O group and double bond is present between 4 and 5 positions of steroid nucleus were prepared by Oppenauer oxidation [Eastham, J. F.; Teranishi, R. In *Organic Synthesis*, Cairns, T. L.; Ed; (John Wiley: New York) 1955; 39] of 17-keto-3-hydroxy DHA aldol product in aluminium isopropoxide-cyclohexanone-toluene system.

According to another feature of the present invention the derivatives of the general formula (A) wherein R independently represents hydrogen and $R_6$ independently represent

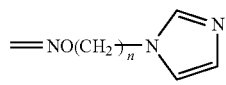

groups and $R_4$=$R_5$=—OCOCH$_3$ or —OH, have been prepared by allylic oxidation of diacetyl derivatives of dehydroepiandrosterone acetate using t-butyl chromate reagent in CCl$_4$ by the method described in the literature (Heusler, K. et al, Helv. Chim. Acta, 1952, 35, 284-294) to form a product wherein $R_6$ represents =O. This was further treated with hydroxylamine hydrochloride to form a derivative with $R_6$ representing =NOH (Singh H et al., Indian J. Chem., 1969, 1084-1087), and then with 1-bromo-3-chloropropane and subsequently thermally fused with imidazole and hydrolysed.

The derivatives of general formulae (A) and (B) wherein R is represented by

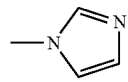

have been prepared by bromination of DHA or indan1-one using cupric bromide by a method previously described in literature (Glazier E R, J. Org. Chem., 1962, 2937-2938) and subsequent thermal fusion with powdered imidazole. Further modifications at $R_4$ and $R_5$ have been carried out as previously described in case of steroidal derivatives.

Biological Activity

The in vitro aromatase inhibitory activity was carried out using human placental microsomes and [1β,2β-$^3$H] testosterone by a method previously described in literature (Graves, P E, Et al, Endocrinology, 1979, 52-57). The imidazolyl substituted Indanones derivatives 2, 4, 6 and 8 displayed good aromatase inhibitory activity with compound 8 (RG-DPJ-195) exhibiting IC$_{50}$=0.55 µM with 50 times greater activity in comparison to aminoglutethimide. These hybrid molecules of Indanones and imidazole resulted in enhanced activity and may have good potential for the treatment of breast cancer. The imidazolyl substituted steroidal derivatives 14, 16, 20, 22, 24, 25, 27 and 30 exhibited significant aromatase inhibitory activity. Compound 30 (DPJ-RG-1241) was the most valuable compound of the series with IC$_{50}$=0.18 µM and relative potency 165 in comparison to aminoglutethimide.

Following examples are given by way of illustration and should not construed to limit the scope of the invention.

EXAMPLE-1 a) 3-(3-Chloropropoxy)benzaldehyde

To a stirred and refluxing suspension of 3-hydroxybenzaldehyde (1.0 g, 8.19 mmol) and potassium carbonate (2 g) in ethyl methyl ketone, 1-bromo-3-chloropropane was added and reaction mixture was allowed to reflux with stirring on oil bath for 6 h. The completion of reaction was monitored by TLC. The slurry was filtered and solvent removed under reduced pressure to obtain an oily residue, which was used as such for further reaction [Naruto S, et al., J. Med. Chem. 1982, 25, 1240-1245].

2-(3-chloropropoxy)benzaldehyde, 3-(3-chloropropoxy)-4-methoxybenzaldehyde and 4-(3-chloropropoxy)-3-methoxybenzaldehyde were prepared using corresponding aldehydes such as salicylaldehyde, isovanillin and vanillin. 3-(2-chloroethoxy)-benzaldehyde was prepared by treating 3-hydroxybenzaldehyde with 1-bromo-2-chloroethane using the similar method described above.

b) 2-[3-(3-Chloropropoxy)benzylidene]-indan-1-one (1) (DPJ-RG-1054)

A solution of indan-1-one (0.4 g, 3.03 mmol) and sodium hydroxide (0.6 g, 15 mmol) in methanol (25 ml) was added to the solution of 3-(3-chloropropoxy)benzaldehyde in methanol (10 ml). The resulting solution was shaken for 30 min and allowed to stand at room temperature with intermittent shaking. The completion of reaction was monitored by TLC. After the completion, excess of methanol was removed; crushed ice was added and allowed to stand overnight. The precipitates obtained were filtered, washed thoroughly with distilled water and dried. The crude product was crystallized from a mixture of acetone and petroleum ether to yield white colored crystals of 2-[3-(3-chloropropoxy)benzylidene]-indan-1-one (1) (0.21 g, 33.5%), mp 73-75° C.

IR (KBr): 2960, 1690, 1590, 1430, 1230 and 740 cm$^{-1}$.
$^1$H-NMR (CDCl$_3$): δ 2.28 (p, 2H, —OCH$_2$CH$_2$—), 3.78 (t, 2H, —CH$_2$Cl), 4.05 (s, 2H, 3-CH$_2$ indanone), 4.18 (t, 2H, —OCH$_2$—), 6.96 (dd, 1H, J$_o$=8.85 Hz, J$_m$=2.43 Hz, aromatic), 7.42 (m, 7H, vinylic-H and aromatic) and 7.91 ppm (d, 1H, J$_o$=7.59 Hz, 7-H Ondanones).

Calcd. For C$_{19}$H$_{17}$O$_2$Cl: C, 72.95; H, 5.47. Found: C, 72.56; H, 5.05.

2-[2-(3-CHLOROPROPOXY)BENZYLIDENE]-INDAN-1-ONE (3) was prepared using 2-(3-chloropropoxy) benzaldehyde following the method described for 1

2-[3-(3-CHLOROPROPOXY)-4-METHOXYBENZYLIDENE]-INDAN-1-ONE (5) was prepared using 3-(3-chloropropoxy) 4-methoxy benzaldehyde following the method described for 1

2-[4-(3-CHLOROPROPOXY)-3-METHOXYBENZYLIDENE]-INDAN-1-ONE (7) (DPJ-1039) was prepared using 4-(3-chloropropoxy)-3-methoxybenzaldehyde following the method described for 1

2-[3-(2-CHLOROETHOXY)BENZYLIDINE]INDAN-1-ONE (9) (RG-DPJ-324) was prepared using 3-(2-chloroethoxy)benzaldehyde following the method described for 1 c) 2-[3-(3-Imidazol-1-yl-propoxy)-benzylidene]-indan-1-one (2) (DPJ-RG-1088)

The compound 2-[3-(3-chloropropoxy)-benzylidene]-indan-1-one (1) (1 g) was triturated with imidazole (1.5 g) and heated at 80-85° C. with stirring for 1 h. The reaction mixture was cooled and distilled water was added to it. Water was then decanted and the solid mass was allowed to dry which was then crystallized from solvent ether to give the compound 2 (0.51 g, 46.59%), mp 48-50° C.

Anal:
IR (KBr): 2940, 1690, 1610, 1240, 1085 and 740 cm$^{-1}$.
$^1$H-NMR (CDCl$_3$): δ 2.27 (p, 2H, —OCH$_2$CH$_2$—), 3.96 (t, 2H, —CH$_2$N), 4.03 (s, 2H, 3-CH$_2$ indanone), 4.22 (t, 2H, —OCH$_2$—), 6.94 (m, 2H, aromatic and imidazolyl), 7.07 (s, 1H, aromatic), 7.16 (s, 1H, aromatic), 7.35 (m, 3H, two aromatic and one imidazolyl), 7.50 (s, 1H, imidazolyl), 7.58 (m, 3H, aromatic (Ondanones) and vinylic-H) and 7.92 ppm (d, 1H, J$_o$=7.53 Hz, 7-CH Ondanones)

Calcd. For C$_{22}$H$_{20}$O$_2$N$_2$: C, 76.72; H, 5.85; N, 8.16. Found: C, 76.68; H, 5.86; N, 8.10.

2-[2-(3-IMIDAZOL-1-YL-PROPOXY)-BENZYLIDINE]-INDAN-1-ONE (4) (DPJ-1055) was prepared by fusing compound 3 with imidazole following the method described for 2

2-[3-(3-IMIDAZOL-1 YL PROPOXY)-4-METHOXY-BENZYLIDENE)INDAN-1-ONE (6) (DPJ-RG-1090) was prepared by fusing compound 5 with imidazole following the method described for 2

2-[4-(3-IMIDAZOL-1YL PROPOXY)-3-METHOXY-BENZYLIDENE)INDAN-1-ONE (8) (RG-DPJ-195) was prepared by fusing compound 7 with imidazole following the method described for 2

2-[3-(2-IMIDAZOL-1YL ETHOXY)-BENZYLIDINE] INDAN-1-ONE (10) (RG-DPJ-325) was prepared by fusing compound 9 with imidazole following the method described for 2

EXAMPLE-2 a) 16-[4-(3-Chloropropoxy)-3-methoxybenzylidene]-17-oxo-5-androsten-3β-ol (11) (DPJ-RG-1150)

A mixture of dehydroepiandrosterone (0.75 g, 2.60 mmol), above obtained oily residue of 4-(3-chloropropoxy)-3-methoxybenzaldehyde and sodium hydroxide (1 g) in methanol (10 Ml) was stirred at room temperature for 2 h and the completion of reaction was monitored by TLC. The product was precipitated by addition of cold water and the precipitate obtained was filtered, washed with water, dried and crystallized from methanol to yield 16-[4-(3-chloropropoxy)-3-methoxybenzylidene]-17-oxo-5-androsten-3β-ol (11) (1 g, 76.96%), mp 210-212° C.

Spectral and Elemental Analyses:
Uvmax (MeOH): 243.0 nm (log ε 4.02) and 331.0 nm (log ε 4.36).

FTIRvmax (KBr): 3220.0, 2922.9, 2829.3, 1709.1, 1623.3, 1593.5, 1515.8, 1447.7, 1325.7, 1260.0, 1140.6, 1094.1, 1057.5, 1023.7, 916.4 and 806.0 cm$^{-1}$.

1H NMR (CDCl3): δ 0.98 (s, 3H, 18-CH$_3$), 1.08 (s, 3H, 19-CH$_3$), 2.31 (m, 2H, —OCH$_2$CH$_2$CH$_2$Cl), 3.53 (m, 1H, 3α-H), 3.77 (t, 2H, —CH$_2$Cl), 3.89 (s, 3H, —OCH$_3$), 4.21 (t, 2H, —OCH$_2$—), 5.40 (d, 1H, 6-CH), 6.95 (d, 1H, J$_o$=8.27 Hz, 5-CH, aromatic), 7.06 (d, 1H, J$_m$=1.73 Hz, 2-CH, aromatic), 7.16 (dd, 1H, J$_m$=1.73 Hz, J$_O$=8.45 Hz, 6-CH, aromatic) and 7.38 ppm (s, 1H, vinylic-H, 16-arylidene).

Calcd. For C$_{30}$H$_{39}$O$_4$Cl: C, 72.20; H, 7.88. Found: C, 72.40; H, 8.02.

b) 16-[3-(3-CHLOROPROPOXY)BENZYLIDENE]-17-OXO-5-ANDROSTEN-3β-OL (17) (DPJ-RG-1306) was Prepared Using 3-(3-chloropropoxy)benzaldehyde Following the Method Described for 11 c) 16-[4-{3-(Imidazol-1-yl)propoxy}-3-methoxybenzylidene]-17-oxo-5-androst-en-3β-ol (12) (DPJ-RG-1151)

A mixture of 16-[4-(3-chloropropoxy)-3-methoxybenzylidene]-17-oxo-5-androsten-3β-ol (11) (0.5 g, 1 mmol) and powdered imidazole (0.75 g) was fused at 110-120° C. for 5 h. The completion of reaction was monitored by TLC. The reaction was quenched with cold water and solid obtained was filtered, washed with water, dried and crystallized from ethyl acetate to yield 12 (0.38 g, 71.47%), mp 199-201° C.
Spectral and Elemental Analyses:
UV$_{max}$ (MeOH): 243.4 nm (log ε 4.04) and 330.8 (log ε 4.39).

FTIRv$_{max}$ (KBr): 3215.3, 2934.3, 1700.9, 1593.4, 1514.3, 1463.0, 1329.9, 1260.4, 1143.7, 1066.5, 917.2 and 832.0 cm$^{-1}$.

¹H NMR (CDCl₃): δ 0.98 (s, 3H, 18-CH₃), 1.07 (s, 3H, 19-CH₃), 2.30 (m, 2H, —OCH₂CH₂CH₂N<), 3.54 (m, 1H, 3α-H), 3.91 (s, 3H, —OCH₃), 3.97 (t, 2H, —CH₂N<), 4.23 (t, 2H, —OCH₂—), 5.39 (d, 1H, 6-CH), 6.85 (d, 1H, $J_o$=8.33 Hz, 5-CH, aromatic), 6.93 (s, 1H, 5-CH, imidazole), 7.06 (d, 2H, 2-CH, aromatic and 4-CH, imidazole), 7.13 (d, 1H, $J_o$=8.26 Hz, 6-CH, aromatic), 7.38 (s, 1H, vinylic-H, 16-arylidene) and 7.48 ppm (s, 1H, 2-CH, imidazole).

Calcd. For $C_{33}H_{42}N_2O_4$: C, 74.68; H, 7.98; N, 5.28. Found: C, 74.62; H, 7.82; N, 5.31.

16-[3-{3-(IMIDAZOL-1-YL)PROPOXY}BENZYLIDENE]-17-OXO-5-ANDRO-STEN-3β-OL (18) (DPJ-RG-1307) was prepared by fusing compound 17 with imidazole following the method described for 12 d) 16-[4-{3-(Imidazol-1-yl)propoxy}-3-methoxybenzylidene]-17-oxo-5-androsten-3β-yl Acetate (13) (DPJ-RG-1196)

A mixture of 16-[4-{3-(imidazol-1-yl)propoxy}-3-methoxybenzylidene]-17-oxo-5-androsten-3β-ol (12) (0.5 g, 0.94 mmol), acetic anhydride (1 Ml) and dry pyridine (2 Ml) was heated in a steam bath for 2 h. The reaction contents were then poured into cold water and basified with liquid ammonia. The precipitate obtained was filtered, washed with water, dried and crystallized from n-hexane to afford 13 (0.27 g, 50.04%), mp 109-111° C.

Spectral and Elemental Analyses:

$UV_{max}$ (MeOH): 249.0 nm (log ε 4.06) and 331.0 nm (log ε 4.30).

$FTIRv_{max}$ (KBr): 2942.1, 1729.7, 1628.3, 1596.2, 1513.2, 1465.7, 1371.4, 1325.6, 1248.5, 1139.4, 1095.7, 1029.7, 915.1 and 812.7 cm⁻¹.

¹H NMR (CDCl₃): δ 0.98 (s, 3H, 18-CH₃), 1.09 (s, 3H, 19-CH₃), 2.04 (s, 3H, —OCOCH₃), 2.29 (m, 2H, —OCH₂CH₂CH₂N<), 3.91 (s, 3H, —OCH₃), 3.98 (t, 2H, —CH₂N<), 4.23 (t, 2H, —OCH₂—), 4.61 (m, 1H, 3α-H), 5.42 (d, 1H, 6-CH), 6.85 (d, 1H, $J_o$=8.48 Hz, 5-CH, aromatic), 6.93 (s, 1H, 5-CH, imidazole), 7.07 (m, 2H, 2-CH, aromatic and 4-CH, imidazole), 7.12 (dd, 1H, $J_m$=1.44 Hz, $J_o$=8.26 Hz, 6-CH, aromatic), 7.38 (s, 1H, vinylic-H, 16-arylidene) and 7.50 ppm (s, 1H, 2-CH, imidazole).

Calcd. For $C_{35}H_{44}N_2O_5$: C, 73.40; H, 7.74; N, 4.89. Found: C, 73.52; H, 7.95; N, 5.01.

16-[3-{3-(IMIDAZOL-1-YL)PROPOXY}BENZYLIDENE]-17-OXO-5-ANDRO-STEN-3β-YL ACETATE (19) (DPJ-RG-1309) was prepared by acetylation of 18 using the method described for compound 13 e) 16-[4-{3-(Imidazol-1-yl)propoxy}-3-methoxybenzylidene]-5-androstene-3β,1β-diol (14) (DPJ-RG-1219)

To a stirred suspension of 16-[4-{3-(imidazol-1-yl)propoxy}-3-methoxy benzylidene]-17-oxo-5-androsten-3β-ol (12) (1 g, 1.88 mmol) in methanol (100 Ml) at room temperature, sodium borohydride (1.5 g) was added in small fractions over a period of 2 h. The reaction mixture was further stirred for 6 h. Solvent was removed under reduced pressure and iced water was added to it. The precipitate obtained was filtered, washed with water, dried and crystallized from methanol to yield the product 14 (0.85 g, 84.68%), mp 197-198° C.

Spectral and Elemental Analyses:

$UV_{max}$ (MeOH): 263.6 nm (log ε 4.02).

$FTIRv_{max}$ (KBr): 3235.9, 2928.7, 1599.3, 1514.0, 1463.4, 1410.2, 1323.1, 1258.8, 1231.7, 1167.5, 1140.4, 1079.6, 1052.1, 949.1, 915.6 and 798.0 cm⁻¹.

¹H NMR (CDCl₃): δ 0.72 (s, 3H, 18-CH₃), 1.05 (s, 3H, 19-CH₃), 2.25 (m, 2H, —OCH₂CH₂CH₂N<), 3.53 (m, 1H, 3α-H), 3.89 (s, 3H, —OCH₃), 3.95 (t, 2H, —CH₂N<), 4.06 (s, 1H, 17α-H), 4.23 (t, 2H, —OCH₂—), 5.38 (d, 1H, 6-CH), 6.45 (s, 1H, vinylic-H, 16-arylidene), 6.81 (m, 1H, 5-CH, aromatic), 6.93 (m, 3H, 2-CH, 6-CH, aromatic and 5-CH, imidazole), 7.07 (s, 1H, 4-CH, imidazole) and 7.54 ppm (s, 1H, 2-CH, imidazole).

Calcd. For $C_{33}H_{44}N_2O_4$: C, 74.40; H, 8.33; N, 5.26. Found: C, 74.27; H, 8.39; N, 5.39.

16-[3-{3-(IMIDAZOL-1-YL)PROPOXY}BENZYLIDENE]-5-ANDROSTENE-3β,17β-DIOL (20) (DPJ-RG-1310) was prepared by sodium borohydride reduction of 18 using a method as described for 14 f) 16-[4-{3-(Imidazol-1-yl)propoxy}-3-methoxybenzylidene]-5-androstene-3β,1β-diol Diacetate (15) (DPJ-RG-1227)

A mixture of 16-[4-{3-(imidazol-1-yl)propoxy}-3-methoxybenzylidene]-5-androstene-3β,17β-diol (14), 0.5 g, 0.94 mmol), acetic anhydride (1 Ml) and dry pyridine (2 Ml) was heated in a steam bath for 2 h. Contents of the reaction mixture were poured into cold water and basified with liquid ammonia. The precipitate obtained was collected by filtration, washed with water, dried and crystallized from n-hexane to furnish the product 15 (0.38 g, 65.64%), mp 163-165° C.

Spectral and Elemental Analyses:

$UV_{max}$ (MeOH): 263.8 nm (log ε 4.28).

$FTIRv_{max}$ (KBr): 2938.9, 1733.7, 1595.9, 1512.1, 1443.3, 1371.1, 1239.5, 1141.3, 1034.2 and 804.5 cm⁻¹.

¹H NMR (CDCl₃): δ 0.80 (s, 3H, 18-CH₃), 1.05 (s, 3H, 19-CH₃), 2.04 (s, 3H, 3β-OCOCH₃), 2.22 (s, 3H, 17β-OCOCH₃), 2.26 (m, 2H, —OCH₂CH₂CH₂N<), 3.89 (s, 3H, —OCH₃), 3.95 (t, 2H, —CH₂N<), 4.23 (t, 2H, —OCH₂—), 4.61 (m, 1H, 3α-H), 5.37 (s, 1H, 17α-H), 5.40 (d, 1H, 6-CH), 6.15 (d, 1H, vinylic-H, 16-arylidene), 6.80 (d, 1H, $J_o$=8.08 Hz, 5-CH, aromatic), 6.89 (s, 2H, 2-CH, aromatic and 5-CH, imidazole), 6.93 (dd, 1H, $J_m$=1.78 Hz, $J_o$=8.86 Hz, 6-CH, aromatic), 7.06 (s, 1H, 4-CH, imidazole) and 7.54 ppm (s, 1H, 2-CH, imidazole).

Calcd. For $C_{37}H_{48}N_2O_6$: C, 72.05; H, 7.84; N, 4.54. Found: C, 72.14; H, 7.72; N, 4.66.

16-[3-{3-(IMIDAZOL-1-YL)PROPOXY}BENZYLIDENE]-5-ANDROSTENE-3β,17β-DIOL DIACETATE (21) (DPJ-RG-1311) was prepared by acetylation of 20 by a method described for 15 g) 16-[4-{3-(Imidazol-1-yl)propoxy}-3-methoxybenzylidene]-4-androstene-3,1-dione (16) (DPJ-RG-1177)

16-[4-{3-(Imidazol-1-yl)propoxy}-3-methoxybenzylidene]-17-oxo-5-androsten-3β-ol (12) (1 g, 1.88 mmol) was dissolved in a mixture of cyclohexanone (10 Ml) and dry toluene (150 Ml). Traces of moisture were removed by azeotropic distillation. The distillation was continued at a slow rate while adding a solution of aluminium isopropoxide (1 g) in dry toluene (15 Ml) drop wise. The reaction mixture was refluxed for 4 h. The slurry was filtered and the residue was washed thoroughly with dry toluene. The combined filtrate and the washings were steam distilled until the removal of organic solvents was affected. The crystalline solid was filtered, washed with water, dried and treated with diethyl ether and n-hexane to afford the required product 16 (0.75 g, 75.28%), mp 107-109° C.

Spectral and Elemental Analyses:

$UV_{max}$ (MeOH): 242.4 nm (log ∈ 4.38) and 331.2 nm (log ∈ 4.30).

$FTIRv_{max}$ (KBr): 2936.4, 1712.0, 1666.1, 1622.3, 1595.3, 1512.2, 1463.2, 1328.4, 1260.2, 1230.4, 1141.7, 1094.2, 1027.4, 917.7 and 810.6 $cm^{-1}$.

$^1$H NMR (CDCl$_3$): δ 1.01 (s, 3H, 18-CH$_3$), 1.25 (s, 3H, 19-CH$_3$), 2.26 (m, 2H, —OCH$_2$CH$_2$CH$_2$N<), 3.92 (s, 3H, —OCH$_3$), 3.97 (t, 2H, —CH$_2$N<), 4.24 (t, 2H, —OCH$_2$—), 5.76 (s, 1H, 4-CH), 6.85 (d, 1H, $J_o$=8.30 Hz, 5-CH, aromatic), 6.94 (s, 1H, 5-CH, imidazole), 7.06 (m, 2H, 2-CH, aromatic and 4-CH, imidazole), 7.13 (dd, 1H, $J_m$=1.27 Hz, $J_o$=8.20 Hz, 6-CH, aromatic), 7.39 (s, 1H, vinylic-H, 16-arylidene) and 7.50 ppm (s, 1H, 2-CH, imidazole).

Calcd. For $C_{33}H_{40}N_2O_4$: C, 74.97; H, 7.63; N, 5.30. Found: C, 74.82; H, 7.66; N, 5.49.

16-[3-{3-(IMIDAZOL-1-YL)PROPOXY}BENZYLIDENE]-4-ANDROSTENE-3,1-DIONE (22) (DPJ-RG-1308) was prepared by Oppeneaur oxidation of 18 by a method as described for 16

EXAMPLE 3 a) 5-Androstene-3β,17β-diol

Sodium borohydride (0.06 g) was added in small portions to a solution of DHA (1 g, 3.47 mmol) in absolute alcohol (50 Ml) at room temperature. The resulting solution was cooled and then neutralized with dilute acetic acid. The solution was concentrated under reduced pressure and diluted with iced water. The curdy white precipitate obtained was crystallized from methanol to obtain the product 5-androstene-3β,17β-diol (0.9 g, 89.11%), mp 182-183° C. [Singh H., et al Indian J. Chem. 1969, 7, 1084-1087].

b) 5-Androstene-3β,17β-diol Diacetate

A mixture of 5-androstene-3β,17β-diol (1 g, 3.44 mmol), acetic anhydride (2 Ml) and dry pyridine (4 Ml) was heated in a steam bath for 2 h, and poured into iced water. The precipitate was filtered, washed with water, dried and crystallized in methanol to afford the product 5-androstene-3β,17β-diol diacetate (1 g, 81.3%), mp 163-165° C. [Singh H., et al Indian J. Chem. 1969, 7, 1084-1087].

c) 7-Oxo-5-androstene-3β,17β-diol Diacetate

A solution of 5-androstene-3β,17β-diol diacetate (5 g, 13.35 mmol) in a mixture of dry carbon tetrachloride (30 Ml), acetic anhydride (4.5 Ml) and glacial acetic acid (1.25 Ml) was treated while stirring with t-butyl chromate solution (35 Ml). The brown reaction mixture was brought to reflux temperature and further stirred for 12 h. The mixture was then cooled in an ice bath and treated in small portions with 10% oxalic acid solution (75 Ml). After adding a further quantity of solid oxalic acid (5.5 g), the reaction mixture was stirred for 2 h at room temperature. The organic phase was removed and the aqueous phase was extracted with carbon tetrachloride (4×50 Ml). The combined carbon tetrachloride extract was successively washed with 5% sodium carbonate solution (2×25 Ml), water and dried. Removal of solvent under reduced pressure gave a pale yellow solid, which was crystallized from methanol to afford the product 7-oxo-5-androstene-3β,17β-diol diacetate (3.2 g, 61.66%), mp 220-221° C. (lit 216-219° C.) [Singh. H., et al Indian J. Chem. 1969, 7, 1084-1087].

d) 7-Oximino-5-androstene-3β,17β-diol Diacetate

7-Oxo-5-androstene-3β,17β-diol diacetate (1 g, 2.57 mmol) and hydroxylamine hydrochloride (0.5 g) were taken in dry pyridine (8 Ml) and heated in a steam bath for 2 h. The reaction mixture was poured into water and precipitate obtained was filtered, washed with water and dried. The crude product on crystallization from methanol afforded pure oxime 7-oximino-5-androstene-3β,17β-diol diacetate (0.85 g, 86.54%), mp 236-238° C. (lit 226° C.) [Singh H., et al Indian J. Chem. 1969, 7, 1084-1087].

Spectral and Elemental Analyses:

$^1$H NMR (CDCl$_3$): δ 0.82 (s, 3H, 18-CH$_3$), 1.14 (s, 3H, 19-CH$_3$), 2.04 (s, 6H, 2× —OCOCH$_3$), 4.67 (m, 2H, 3α-H and 17α-H), 6.46 (s, 1H, 6-CH) and 6.95 ppm (br, 1H, NOH, disappeared on adding D$_2$O).

e) 7-[O-(3-Chloropropyl)oximino]-5-androstene-3β,17β-diol Diacetate (23) (DPJ-RG-1221)

A mixture of 7-oximino-5-androstene-3β,17β-diol diacetate (1 g, 2.48 mmol) and anhydrous potassium carbonate (2 g) was stirred and refluxed in ethyl methyl ketone (100 Ml) at 110° C. for 3 h. 1-Bromo-3-chloropropane (0.25 Ml, 2.48 mmol) was added to the reaction mixture and further refluxed for 20 h with continuous stirring. The completion of the reaction was monitored by TLC. The slurry was cooled, filtered and excess of solvent was removed under reduced pressure to obtain an oily residue. Iced water was added to the oily residue and it was allowed to stand overnight. The precipitate obtained was filtered, washed with water, dried and crystallized from pet-ether (60-80° C.) to afford 7-[O-(3-chloropropyl)oximino]-5-androstene-3β,17β-diol diacetate (23) (0.7 g, 58.82%), mp 155° C. (Decomp).

Spectral and Elemental Analyses:

$UV_{max}$ (MeOH): 241.4 nm (log ∈ 4.16).

$FTIRv_{max}$ (KBr): 2945.5, 2878.1, 1736.5, 1640.6, 1450.8, 1371.7, 1246.2, 1033.4, 953.2, 909.3 and 840.0 $cm^{-1}$.

$^1$H NMR (CDCl$_3$): δ 0.81 (s, 3H, 18-CH$_3$), 1.13 (s, 3H, 19-CH$_3$), 2.03 (s, 6H, 2× —OCOCH$_3$), 2.10 (m, 2H, —OCH$_2$CH$_2$CH$_2$Cl), 3.60 (t, 2H, —CH$_2$Cl), 4.14 (t, 2H, —OCH$_2$—), 4.64 (m, 2H, 3α-H and 17α-H) and 6.43 ppm (d, 1H, 6-CH).

Calcd. For $C_{26}H_{38}NO_5Cl$: C, 65.05; H, 7.98; N, 2.92. Found: C, 65.32; H, 8.18; N, 2.69.

f) 7-[O-{3-(Imidazol-1-yl)propyl}oximino]-5-androstene-3β,17μ-diol (25) (DPJ-RG-1223)

A mixture of 7-[O-(3-chloropropyl)oximino]-5-androstene-3β,17β-diol diacetate (23) (1 g, 2.08 mmol) and powdered imidazole (1.5 g) was fused at 110-120° C. for 5 h. The completion of reaction was monitored by TLC. The reaction was quenched with iced water to afford a the product 7-[O-{3-(imidazol-1-yl)propyl}oximino]-5-androstene-3β,17β-diol diacetate (24)

To the refluxing solution of 7-[O-{3-(imidazol-1-yl)propyl}oximino]-5-androstene-3β,17β-diol diacetate in methanol (50 Ml), potassium hydroxide (0.125 g) was added and the reaction mixture was further refluxed for 45 min. The reaction mixture was concentrated, acidified with glacial acetic acid and poured into cold water. The precipitate obtained was filtered, washed thoroughly with water, dried and crystallized from diethyl ether to furnish the product 25 (0.25 g, 23.45%), mp 205-206° C.

Spectral and Elemental Analyses:

$UV_{max}$ (MeOH): 258.2 nm (log ε 4.17).

$FTIRv_{max}$ (KBr): 3301.5, 3107.3, 2940.0, 2871.2, 1631.3, 1511.8, 1456.6, 1377.7, 1231.1, 1187.9, 1081.6, 1059.7, 1025.6, 952.0, 921.8, 889.0 and 823.3 $cm^{-1}$.

$^1$H NMR ($CDCl_3$): δ 0.78 (s, 3H, 18-$CH_3$), 1.13 (s, 3H, 19-$CH_3$), 2.37 (m, 2H, —$OCH_2CH_2CH_2$N<), 3.65 (m, 2H, 3α-H and 17α-H), 4.03 (m, 4H, —$OCH_2CH_2CH_2$N<), 6.39 (d, 1H, 6-CH), 6.95 (brs, 5-CH, imidazole), 7.07 (brs, 4-CH, imidazole) and 7.49 ppm (brs, 2-CH, imidazble).

Calcd. For $C_{25}H_{37}N_3O_3$: C, 70.23; H, 8.72; N, 9.83. Found: C, 70.19; H, 8.94; N, 9.76.

EXAMPLE 4 a) 16α-Bromo-17-oxo-5-androsten-3β-ol

Cupric bromide (7 g) was added to a refluxing solution of 17-oxo-5-androsten-3β-ol (5 g, 17.33 mmol) in dry benzene (100 Ml) and dry methanol (100 Ml). The reaction mixture was further refluxed for 4 h and the reaction was monitored with TLC. The warm solution was filtered and concentrated to about two-third volume under reduced pressure. The remaining solvent was diluted with benzene (50 Ml) and washed twice with water. The benzene layer was collected, dried and the solvent removed under reduced pressure to obtain a residue, which was crystallized from methanol to afford the product 16α-bromo-17-oxo-5-androsten-3β-ol (4 g, 62.77%), mp 167-168° C. (lit 164-165° C.) [Glazier E R, J. Org. Chem., 1962, 2937-2938].

$^1$H NMR ($CDCl_3$): δ 0.93 (s, 3H, 18-$CH_3$), 1.04 (s, 3H, 19-$CH_3$), 3.55 (m, 1H, 3α-H), 4.55 (t, 1H, 16β-CH) and 5.38 ppm (m, 1H, 6-CH).

2-Bromo-1-Indanone (31) was prepared by bromination of 1-indanone with cupric bromide following the method as described by Glazier E R. J. Org. Chem., 1962, 2937-2938.

b) 16α/β-Bromo-4-androstene-3,17-dione (26)

16α-Bromo-17-oxo-5-androsten-3β-ol (1 g, 2.72 mmol) was dissolved in a mixture of cyclohexanone (10 Ml) and dry toluene (100 Ml). Traces of moisture were removed by azeotropic distillation of toluene. The distillation was continued at a slow rate while adding a solution of aluminium isopropoxide (1 g) in dry toluene (20 Ml) dropwise. The reaction mixture was refluxed for 1 h and allowed to stand at room temperature overnight. The slurry was filtered and the residue was washed with dry toluene. The combined filtrate and the washings were steam distilled until the complete removal of organic solvents was affected. The solid obtained was filtered, washed with water, dried and crystallized from a mixture of acetone and n-hexane to yield the product 16α/β-bromo-4-androstene-3,17-dione (26) (0.6 g, 60.33%), mp 128-130° C.

Spectral Analyses:

$UV_{max}$ (MeOH): 238.8 nm (log ε 4.22).

IR (KBr): 2930.0, 1748.5, 1667.2, 1612.1, 1453.5, 1228.6 and 1017.9 $cm^{-1}$ $^1$H NMR ($CDCl_3$): δ 1.13 (s, 3H, 18-$CH_3$), 1.22 (s, 3H, 19-$CH_3$), 4.12 (t) and 4.56 (q) (3.5:1 area ratio, 1H, 16α-H and 16β-H) and 5.76 ppm (s, 1H, 4-CH).

c) 16β-(Imidazol-1-yl)-17-oxo-5-androsten-3β-ol (27) (DPJ-RG-1240)

A mixture of 16α-bromo-17-oxo-5-androsten-3β-ol (1 g, 2.72 mmol) and imidazole (1.5 g) was heated at 140-145° C. for 1 h. The reaction mixture was cooled to room temperature and precipitated with iced water. The solid obtained was filtered, washed with water, dried and crystallized from acetone to yield 27 (0.5 g, 51.81%), mp 249-251° C.

Spectral and Elemental Analyses:

$FTIRv_{max}$ (KBr): 3303.8, 2943.0, 1744.8, 1499.5, 1456.1, 1374.7, 1318.3, 1243.9, 1065.8, 1041.4 and 914.2 $cm^{-1}$.

$^1$H NMR ($CDCl_3$): δ 1.02 (s, 3H, 18-$CH_3$), 1.07 (s, 3H, 19-$CH_3$), 3.55 (m, 1H, 3α-H), 4.47 (m, 1H, 16α-H), 5.39 (d, 1H, 6-CH), 6.95 (s, 1H, 5-CH, imidazole), 7.12 (s, 1H, 4-CH, imidazole) and 7.70 ppm (s, 1H, 2-CH, imidazole).

Calcd for $C_{22}H_{30}N_2O_2$: C, 74.54; H, 8.53; N, 7.90. Found: C, 74.29; H, 9.04; N, 7.73.

2-(1H-1-imidazolyl)-1-indanone (32) was prepared by fusing imidazole with 31 as described for compound 27.

d) 16β-(Imidazol-1-yl)-5-androstene-3β,17β-diol (28) (DPJ-RG-1317)

To a stirred suspension of 16β-(imidazol-1-yl)-17-oxo-5-androsten-3β-ol (27), (1 g, 2.82 mmol) in methanol (100 Ml) at room temperature, sodium borohydride (1.5 g) was added in small fractions over a period of 2 h. The reaction mixture was further stirred for 4 h. Solvent was removed under reduced pressure and cold water was added. The precipitate obtained was filtered, washed with water, dried and crystallized from methanol to afford 28 (0.75 g, 74.57%), mp 285-287° C.

Spectral and Elemental Analyses:

$FTIRv_{max}$ (KBr): 3259.0, 2930.9, 1501.4, 1459.5, 1365.1, 1235.8, 1152.7, 1083.2 and 955.1 $cm^{-1}$.

$^1$H NMR ($CDCl_3$): δ 0.89 (s, 3H, 18-$CH_3$), 1.03 (s, 3H, 19-$CH_3$), 3.43 (m, 1H, 3α-H), 3.79 (m, 1H, 17α-H), 4.59 (q, 1H, 16α-H), 5.32 (d, 1H, 6-CH), 6.97 (s, 1H, 5-CH, imidazole), 7.04 (s, 1H, 4-CH, imidazole) and 7.59 ppm (m, 1H, 2-CH, imidazole).

Calcd for $C_{22}H_{32}N_2O_2$: C, 74.12; H, 9.05; N, 7.86. Found: C, 74.39; H, 9.62; N, 8.02.

e) 16β-(Imidazol-1-yl)-5-androstene-3β,17β-diol Diacetate (29) (DPJ-RG-1318)

A mixture of 16β-(imidazol-1-yl)-5-androstene-3β,17β-diol 28 (1 g, 2.80 mmol), acetic anhydride (2 Ml) and dry pyridine (2 Ml) was heated in a steam bath for 2 h. The reaction mixture was then poured into cold water and basified with liquid ammonia. The precipitate formed was collected by filtration, washed with water, dried and crystallized from acetone to afford 29 (0.8 g, 64.72%), mp 197-199° C.

Spectral and Elemental Analyses:

$FTIRv_{max}$ (KBr): 2937.5, 1732.9, 1494.1, 1435.5, 1371.8, 1250.1, 1072.9, 1037.7 and 906.0 $cm^{-1}$.

$^1$H NMR ($CDCl_3$): δ 1.02 (s, 3H, 18-$CH_3$), 1.07 (s, 3H, 19-$CH_3$), 1.74 (s, 3H, 17β-$OCOCH_3$), 2.04 (s, 3H, 3β-$OCOCH_3$), 4.61 (m, 1H, 3α-H), 4.79 (m, 2H, 16α-H and 17α-H), 5.39 (d, 1H, 6-CH), 6.89 (s, 1H, 5-CH, imidazole), 7.02 (s, 1H, 4-CH, imidazole) and 7.48 ppm (s, 1H, 2-CH, imidazole).

Calcd for $C_{26}H_{36}N_2O_4$: C, 70.88; H, 8.24; N, 6.36. Found: C, 70.29; H, 8.95; N, 6.49.

f) 16β-(Imidazol-1-yl)-4-androstene-3,17-dione (30) (DPJ-RG-1241)

A mixture of 16α/β-bromo-4-androstene-3,17-dione (26) (1 g, 2.74 mmol) and imidazole (1.5 g) was triturated and heated at 130-135° C. for 1 h. The reaction mixture was cooled at room temperature and cold water was added to it. The residue obtained was filtered, washed with water, dried and crystallized from a mixture of acetone and n-hexane to afford 30 (0.4 g, 41.45%), mp 179-181° C.

Spectral and Elemental Analyses:

UV$_{max}$ (MeOH): 238.4 (log ϵ 4.31).

FTIRν$_{max}$ (KBr): 2947.6, 1748.7, 1667.5, 1497.7, 1456.0, 1229.8, 1108.9, and 1045.0 cm$^{-1}$.

$^1$H NMR (CDCl$_3$): δ 1.06 (s, 3H, 18-CH$_3$), 1.24 (s, 3H, 19-CH$_3$), 4.46 (m, 1H, 16α-H), 5.76 (s, 1H, 4-CH), 6.95 (s, 1H, 5-CH, imidazole), 7.09 (s, 1H, 4-CH, imidazole) and 7.66 ppm (s, 1H, 2-CH, imidazole).

Calcd for C$_{22}$H$_{28}$N$_2$O$_2$: C, 74.97; H, 8.01; N, 7.95. Found: C, 74.71; H, 8.58; N, 8.12.

Characterization

2-[2-(3-CHLOROPROPOXY)-BENZYLIDENE]-INDAN-1-ONE (3)

Yield=66.46%, mp: 130-134° C.

Anal:

IRν$_{max}$ (KBr): 2970, 1680, 1600, 1440, 1230, 740 cm$^{-1}$.

$^1$H NMR (CDCl$_3$): δ 2.31 (p, 2H, —OCH$_2$CH$_2$CH$_2$Cl—), 3.81 (t, 2H, —CH$_2$Cl), 3.98 (s, 2H, 3-CH$_2$ indanone), 4.19 (t, 2H, —OCH$_2$), 6.96 (d, 1H, J$_o$=8.49 Hz, aromatic), 7.03 (t, 1H, J$_o$=7.52 Hz, aromatic), 7.33 (dd, 1H, J J$_o$=6.83 Hz, aromatic), 7.40 (t, 1H, J$_o$=7.34 Hz, aromatic), 7.59 (m, 3H, aromatic □ndanones), 7.89 (d, 1H, J$_o$=7.61 Hz, 7-H □ndanones), 8.11 (s, 1H, vinylic —H).

Calcd. For C$_{19}$H$_{17}$O$_2$Cl: C, 72.95; H, 5.47. Found: C, 70.31; H, 5.09.

2-[2-(3-IMIDAZOL-1-YL-PROPOXY)-BENZYLIDINE]-INDAN-1-ONE (4) (DPJ-1055)

Yield: 60.3%, mp: 76-78° C.

Anal:

IRν$_{max}$ (KBr): 3360, 1680, 1600, 1140, 750 cm$^{-1}$.

$^1$H NMR (CDCl$_3$): δ 2.31 (p, 2H, —OCH$_2$CH$_2$CH$_2$—), 3.93 (t, 2H, —CH$_2$N), 4.00 (s, 2H, 3-CH$_2$ indanone), 4.26 (t, 2H, —OCH$_2$), 6.87 (d, 1H, J$_o$=8.18 Hz, aromatic), 6.98 (d, 1H, imidazole), 7.39 (m, 8H, aromatic and imidazole), 7.92 (d, 1H, J$_o$=7.76 Hz, 7-H □ndanones), 8.19 (s, 1H, vinylic —H).

Calcd. For C$_{19}$H$_{17}$O$_2$Cl: C, 72.95; H, 5.47. Found: C, 70.31; H, 5.09.

2-[3-(3-CHLOROPROPOXY)-4-METHOXYBENZYLIDENE]-INDAN-1-ONE (5)

Yield=42.86%, mp: 115-118° C.

Anal:

IRν$_{max}$ (KBr): 2900, 1680, 1600, 1260, 1140, 730 cm$^{-1}$.

$^1$H NMR (CDCl$_3$): δ 2.32 (p, 2H, —OCH$_2$CH$_2$CH$_2$—), 3.81 (t, 2H, —CH$_2$Cl), 3.88 (s, 3H, —OCH$_3$), 3.96 (s, 2H, 3-CH$_2$ indanone), 4.23 (t, 2H, —OCH$_2$), 6.95 (d, 1H, J$_o$=8.3 Hz, aromatic), 7.21 (s, 1H, aromatic), 7.29 (dd, 1H, J$_o$=8.56 Hz, J$_m$=1.62 Hz, aromatic), 7.40 (t, 1H, J$_o$=7.10 Hz, aromatic □ndanones), 7.56 (m, 3H, aromatic □ndanones and vinylic-H), 7.88 (d, 1H, J$_o$=7.56 Hz, 7-H □ndanones).

Calcd. For C$_{19}$H$_{17}$O$_2$Cl: C, 72.95; H, 5.47. Found: C, 70.31; H, 5.09.

2-[3-(3-IMIDAZOL-1YL PROPOXY)-4-METHOXYBENZYLIDENE)INDAN-1-ONE (6) (DPJ-RG-1090)

Yield: 55.49%, mp: 176-180° C.

Anal:

IRν$_{max}$ (KBr): 2900, 1680, 1590, 1250, 1070, 740 cm$^{-1}$.

$^1$H NMR (CDCl$_3$): δ 2.30 (p, 2H, —OCH$_2$CH$_2$CH$_2$—), 3.93 (s, 3H, —OCH$_3$), 3.96 (t, 2H, —CH$_2$N), 4.01 (s, 2H, 3-CH$_2$ indanone), 4.26 (t, 2H, —OCH$_2$), 6.96 (d, 1H, J$_o$=8.45 Hz, aromatic and imidazolyl), 7.10 (d, 1H, aromatic), 7.33 (m, 2H, aromatic (□ndanones) and imidazolyl), 7.55 (m, 4H, aromatic (□ndanones), imidazolyl and vinylic-H) and 7.87 ppm (d, 1H, J$_o$=7.53 Hz, 7-CH □ndanones).

Calcd. For C$_{23}$H$_{22}$O$_3$N$_2$: C, 73.78; H, 5.92; N, 7.48. Found: C, 66.90; H, 5.93; N, 6.66.

2-[4-(3-CHLOROPROPOXY)-3-METHOXYBENZYLIDENE]-INDAN-1-ONE (7) (DPJ-1039)

Yield=27.5%, mp: 140-144° C.

Anal:

IRν$_{max}$ (KBr): 2240, 1700, 1605, 1240, 1140 cm$^{-1}$.

$^1$H NMR (CDCl$_3$): δ 2.33 (p, 2H, —OCH$_2$CH$_2$CH$_2$—), 3.79 (t, 2H, —CH$_2$Cl), 3.95 (s, 3H, —OCH$_3$), 4.04 (s, 2H, 3-CH$_2$ of □ndanones), 4.25 (t, 2H, —OCH$_2$), 6.99 (d, 1H, J$_o$=8.41 Hz, aromatic), 7.20 (d, 1H, J$_o$=1.91 Hz, aromatic), 7.31 (dd, 1H, J$_o$=6.58 Hz, J$_m$=1.92 Hz, aromatic), 7.43 (t, 1H, J$_o$=6.96 Hz), 7.59 (m, 3H, aromatic □ndanones and vinylic-H), 7.91 (d, 1H, J$_o$=7.56 Hz, 7-H of □ndanones).

Calcd. For C$_{20}$H$_{19}$O$_3$Cl: C, 70.07; H, 5.58. Found: C, 68.41; H, 4.93.

2-[4-(3-IMIDAZOL-1YL PROPOXY)-3-METHOXYBENZYLIDENE)INDAN-1-ONE (8) (RG-DPJ-195)

Yield: 34.28%; mp, 123-127° C.

Anal:

$^1$H NMR (CDCl$_3$): δ 2.33 (p, 2H, —OCH$_2$CH$_2$CH$_2$—), 3.98 (s, 3H, —OCH$_3$), 4.01 (t, 2H, —OCH$_2$CH$_2$N), 4.29 (t, 2H, —OCH$_2$—), 6.89 (d, 1H, aromatic), 6.99 (s, 1H, imidazolyl proton), 7.12 (s, 1H, aromatic), 7.21 (s, 1H, imidazolyl), 7.21 (s, 1H, aromatic), 7.44 (s, 1H, aromatic), 7.55 (t, 1H, aromatic) and 7.60 ppm (m, 3H, aromatic).

2-[3-(2-CHLOROETHOXY)-BENZYLIDINE]INDAN-1-ONE (9) (RG-DPJ-324)

Yield: 36.74%; mp 136-138° C.

Anal:

IR (KBr): 2955, 1680, 1590, 1420, 1225 and 730 cm$^{-1}$.

$^1$H-NMR (CDCl$_3$): δ 3.88 (t, 2H, —CH$_2$Cl), 4.06 (s, 2H, 3-CH$_2$ indanone), 4.31 (t, 2H, —OCH$_2$—), 6.96 (dd, 1H, J$_o$=8.12 Hz, J$_m$=2.52 Hz, aromatic), 7.22 (t, 1H, J$_m$=2.05 Hz, aromatic), 7.32 (d, 1H, aromatic), 7.40 (t, 2H, aromatic), 7.64 (d, 1H, aromatic), 7.71 (t, 1H, aromatic) and 7.91 ppm (d, 1H, 7-H □ndanones).

2-[3-(2-IMIDAZOL-1YL ETHOXY)-BENZYLIDINE]INDAN-1-ONE (10) (RG-DPJ-325)

Yield: 32.24%; mp 218-220° C.

Anal:

IR (KBr): 2940, 1690, 1610, 1240, 1085 and 740 cm$^{-1}$.

$^1$H-NMR (CDCl$_3$): δ 4.04 (s, 2H, 3-CH$_2$ indanone), 4.30 (t, 2H, —CH$_2$N), 4.42 (t, 2H, —OCH$_2$—), 6.92 (dd, 1H, aromatic J$_o$=8.10 Hz, J$_m$=2.36 Hz), 7.14 (m, 2H, aromatic), 7.36 (m, 3H, aromatic and imidazolyl), 7.51 (m, 3H, aromatic (Indanones) and vinylic-H), 7.57 (s, 1H, imidazolyl) and 7.93 ppm (d, 1H, 7-CH Indanones)

16-[3-(3-CHLOROPROPOXY)BENZYLIDENE]-17-OXO-5-ANDROSTEN-3β-OL (17) (DPJ-RG-1306)

Yield: 40.98%; mp, 145-147° C.

Anal:

FTIR$\nu_{max}$ (KBr): 3419.2, 2932.9, 1715.6, 1628.7, 1580.1, 1445.1, 1375.0, 1257.2, 1215.4, 1163.3, 1054.2, 1008.0, 918.4 and 873.6 cm$^{-1}$.

$^1$H NMR (CDCl$_3$): δ 0.90 (s, 3H, 18-CH$_3$), 1.00 (s, 3H, 19-CH$_3$), 2.19 (m, 2H, —OCH$_2$CH$_2$CH$_2$Cl), 3.40 (m, 1H, 3α-H), 3.67 (t, 2H, —CH$_2$Cl), 4.06 (t, 2H, —OCH$_2$—), 5.27 (d, 1H, 6-CH), 6.79 (d, 1H, J$_o$=8.01 Hz, 4-CH, aromatic), 6.93 (s, 1H, 2-CH, aromatic), 7.02 (d, 1H, J$_o$=7.55 Hz, 6-CH, aromatic) and 7.18-7.24 ppm (m, 2H, 5-CH, aromatic and vinylic-H, 16-arylidene).

Calcd. For C$_{29}$H$_{37}$O$_3$Cl: C, 74.26; H, 7.95. Found: C, 74.64; H, 8.12.

16-[3-{3-(IMIDAZOL-1-YL)PROPOXY}BENZYLIDENE]-17-OXO-5-ANDROSTEN-3β-OL (18) (DPJ-RG-1307)

Yield: 45.87%; mp 211-212° C.

Anal:

FTIR$\nu_{max}$ (KBr): 3253.0, 2932.8, 2837.0, 1713.9, 1629.0, 1576.6, 1448.6, 1385.6, 1269.0, 1160.8, 1067.0, 919.8, 872.7 and 779.6 cm$^{-1}$.

$^1$H NMR (CDCl$_3$): δ 0.98 (s, 3H, 18-CH$_3$), 1.07 (s, 3H, 19-CH$_3$), 2.22 (m, 2H, —OCH$_2$CH$_2$CH$_2$N<), 3.49 (m, 1H, 3α-H), 3.92 (t, 2H, —CH$_2$N<), 4.21 (t, 2H, —OCH$_2$—), 5.35 (s, 1H, 6-CH), 6.84 (dd, 1H, J$_m$=2.17 Hz, J$_o$=8.17 Hz, 4-CH, aromatic) 6.88 (s, 1H, 5-CH, imidazole), 7.02 (m, 2H, 2-CH, aromatic and 4-CH, imidazole), 7.13 (d, 1H, J$_o$=7.64 Hz, 6-CH, aromatic), 7.26-7.34 (m, 2H, 5-CH, aromatic and vinylic-H, 16-arylidene) and 7.44 ppm (s, 1H, 2-CH, imidazole).

Calcd. For C$_{32}$H$_{40}$N$_2$O$_3$: C, 76.77; H, 8.05; N, 5.59. Found: C, 76.85; H, 8.19; N, 5.65.

16-[3-{3-(IMIDAZOL-1-YL)PROPOXY}BENZYLIDENE]-17-OXO-5-ANDROSTEN-3β-YL ACETATE (19) (DPJ-RG-1309)

Yield: 47.16%; mp, 148-150° C.

Anal:

FTIR$\nu_{max}$ (KBr): 2940.6, 1728.2, 1631.8, 1575.8, 1508.0, 1443.8, 1374.8, 1254.0, 1163.7, 1030.5, 908.8 and 873.9 cm$^{-1}$.

$^1$H NMR (CDCl$_3$): δ 0.98 (s, 3H, 18-CH$_3$), 1.09 (s, 3H, 19-CH$_3$), 2.03 (s, 3H, —OCOCH$_3$), 2.23 (m, 2H, —OCH$_2$CH$_2$CH$_2$N<), 3.91 (t, 2H, —CH$_2$N<), 4.21 (t, 2H, —OCH$_2$—), 4.58 (m, 1H, 3α-H), 5.41 (d, 1H, 6-CH), 6.83 (dd, 1H, J$_m$=2.15 Hz, J$_o$=8.11 Hz, 4-CH, aromatic) 6.87 (s, 1H, 5-CH, imidazole), 6.97 (s, 1H, 2-CH, aromatic), 7.02 (s, 1H, 4-CH, imidazole), 7.13 (d, 1H, J$_o$=7.73 Hz, 6-CH, aromatic), 7.30 (m, 2H, 5-CH, aromatic and vinylic-H, 16-arylidene) and 7.43 ppm (s, 1H, 2-CH, imidazole).

Calcd. For C$_{33}$H$_{42}$N$_2$O$_4$: C, 74.69; H, 7.98; N, 5.28. Found: C, 74.82; H, 7.49; N, 5.31.

16-[3-{3-(IMIDAZOL-1-YL)PROPOXY}BENZYLIDENE]-5-ANDROSTENE-3β,17β-DIOL (20) (DPJ-RG-1310)

Yield: 50.2%; mp, 133-135° C.

Anal:

FTIR$\nu_{max}$ (KBr): 3373.7, 2936.1, 1601.2, 1438.1, 1366.7, 1252.4, 1161.9, 1050.8 and 955.5 cm$^{-1}$.

$^1$H NMR (CDCl$_3$): δ 0.72 (s, 3H, 18-CH$_3$), 1.04 (s, 3H, 19-CH$_3$), 2.25 (m, 2H, —OCH$_2$CH$_2$CH$_2$N<), 3.54 (m, 1H, 3α-H), 3.91 (t, 2H, —CH$_2$N<), 4.06 (s, 1H, 17α-H), 4.21 (t, 2H, —OCH$_2$—), 5.38 (d, 1H, 6-CH), 6.48 (d, 1H, vinylic-H, 16-arylidene), 6.73 (dd, 1H, J$_m$=2.29 Hz, J$_o$=8.03 Hz, 4-CH, aromatic), 6.87 (s, 4H, 2-CH, 6-CH, aromatic and 4-CH, 5-CH, imidazole), 7.26 (m, 1H, 5-CH, aromatic) and 7.48 ppm (s, 1H, 2-CH, imidazole).

Calcd. For C$_{32}$H$_{42}$N$_2$O$_3$: C, 76.46; H, 8.42; N, 5.57. Found: C, 76.42; H, 8.59; N, 5.41.

16-[3-{3-(IMIDAZOL-1-YL)PROPOXY}BENZYLIDENE]-5-ANDROSTENE-3β, 17β-DIOL DIACETATE (21) (DPJ-RG-1311)

Yield: 34.48%; mp, 97-99° C.

Anal:

FTIR$\nu_{max}$ (KBr): 2939.5, 1732.6, 1600.5, 1440.4, 1372.0, 1241.2, 1162.1, 1034.7 and 907.6 cm$^{-1}$.

$^1$H NMR (CDCl$_3$): δ 0.79 (s, 3H, 18-CH$_3$), 1.05 (s, 3H, 19-CH$_3$), 2.04 (s, 3H, 3β-OCOCH$_3$), 2.21 (s, 3H, 17β-OCOCH$_3$), 2.32 (m, 2H, —OCH$_2$CH$_2$CH$_2$N<), 3.91 (t, 2H, —CH$_2$N<), 4.20 (t, 2H, —OCH$_2$—), 4.59 (m, 1H, 3α-H), 5.37 (s, 1H, 17α-H), 5.41 (d, 1H, 6-CH), 6.17 (s, 1H, vinylic-H, 16-arylidene), 6.73 (d, 1H, J$_o$=7.96 Hz, 4-CH, aromatic), 6.84 (s, 1H, 2-CH, aromatic), 6.93-7.06 (m, 3H, 6-CH, aromatic and 4-CH, 5-CH, imidazole), 7.26 (m, 1H, 5-CH, aromatic) and 7.49 ppm (s, 1H, 2-CH, imidazole).

Calcd. For C$_{36}$H$_{46}$N$_2$O$_6$: C, 73.69; H, 7.90; N, 4.77. Found: C, 73.51; H, 7.99; N, 4.94.

16-[3-{3-(IMIDAZOL-1-YL)PROPOXY}BENZYLIDENE]-4-ANDROSTENE-3, 1-DIONE (22) (DPJ-RG-1308)

Yield: 50.25%; mp, 81-83° C.

Anal:

FTIR$\nu_{max}$ (KBr): 2937.9, 1717.0, 1663.4, 1622.8, 1576.0, 1448.5, 1256.8, 1226.2, 1179.0, 1162.2, 1080.7, 1026.6, 915.8 and 864.3 cm$^{-1}$.

$^1$H NMR (CDCl$_3$): δ 1.02 (s, 3H, 18-CH$_3$), 1.25 (s, 3H, 19-CH$_3$), 2.26 (m, 2H, —OCH$_2$CH$_2$CH$_2$N<), 3.94 (t, 2H, —CH$_2$N<), 4.23 (t, 2H, —OCH$_2$—), 5.76 (d, 1H, 4-CH), 6.90 (dd, 1H, J$_m$=1.90 Hz, J$_o$=8.12 Hz, 4-CH, aromatic) 6.95 (s, 1H, 5-CH, imidazole), 7.02 (s, 1H, 2-CH, aromatic), 7.08 (s, 1H, 4-CH, imidazole), 7.16 (d, 1H, J$_o$=7.68 Hz, 6-CH, aromatic), 7.33 (t, 1H, J$_o$=7.91 Hz, 5-CH, aromatic), 7.40 (s, 1H, vinylic-H, 16-arylidene) and 7.57 ppm (s, 1H, 2-CH, imidazole).

Calcd. For C$_{32}$H$_{38}$N$_2$O$_3$: C, 77.08; H, 7.68; N, 5.62. Found: C, 77.22; H, 7.49; N, 5.88.

The synthetic routes for the preparation of various compounds have been depicted in schemes 1-5.

Scheme 1
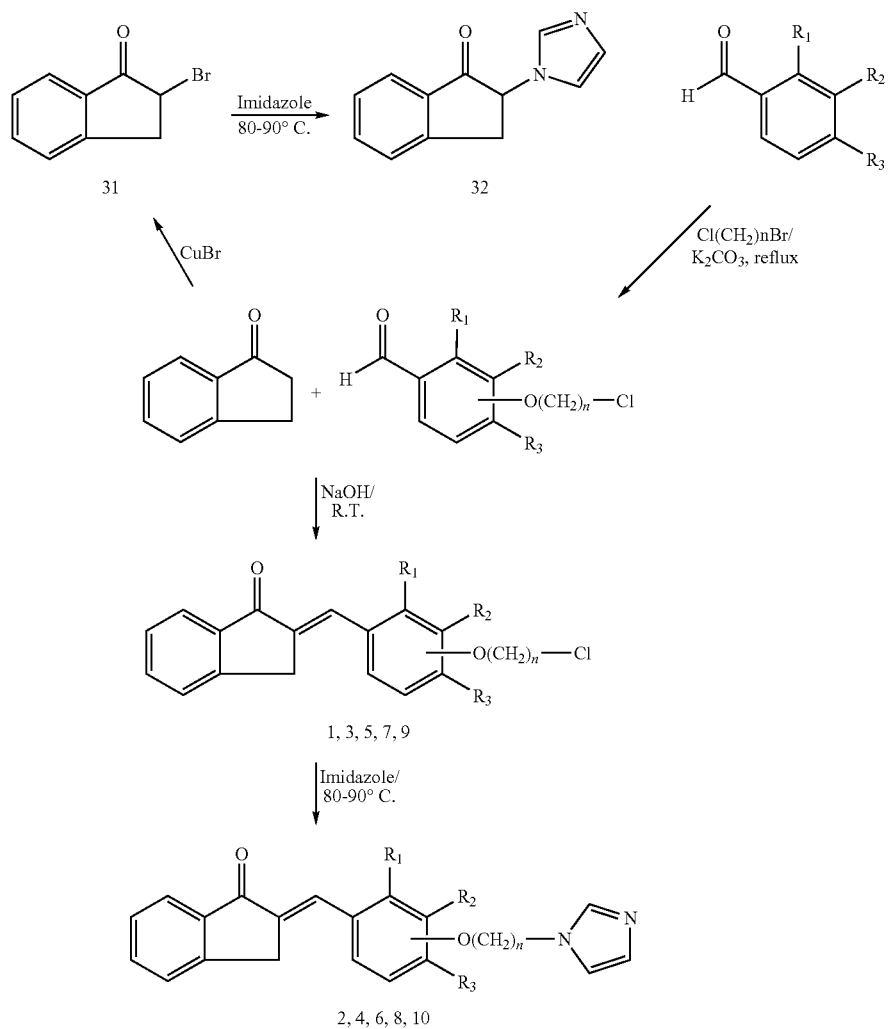
Scheme 2
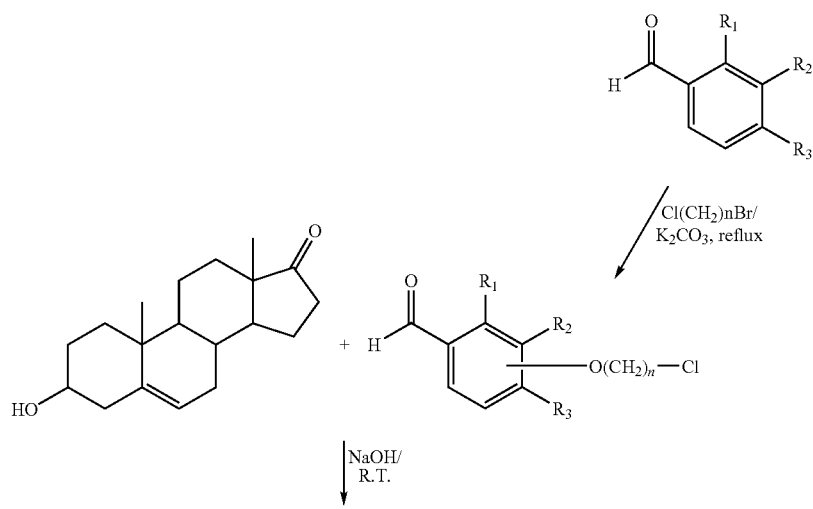

-continued
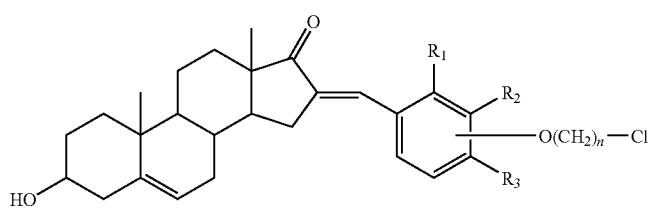
11, 17
↓ Imidazole
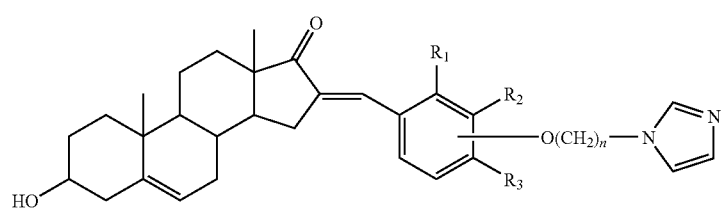
12, 18
Scheme 3
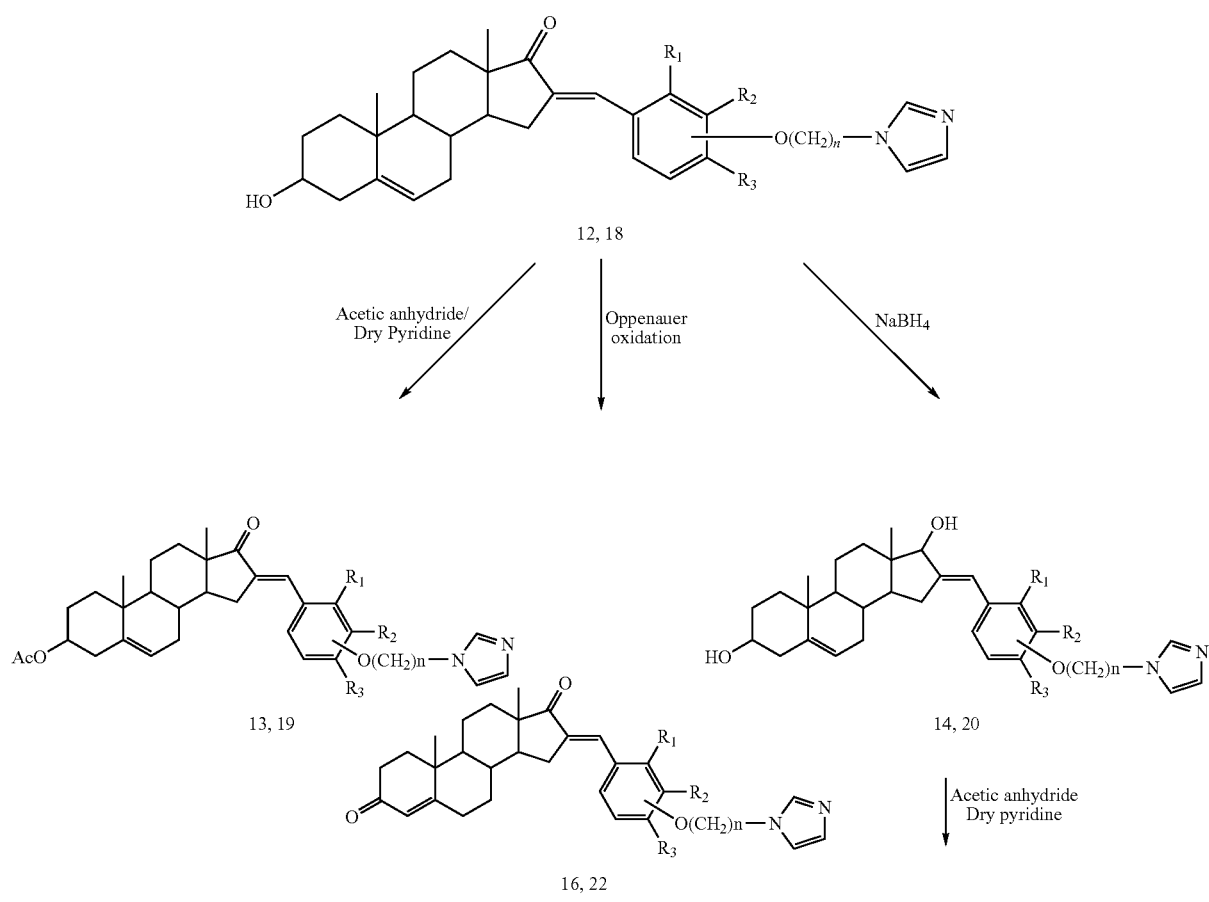

-continued
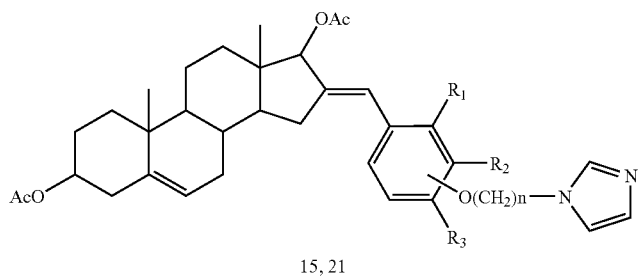
15, 21
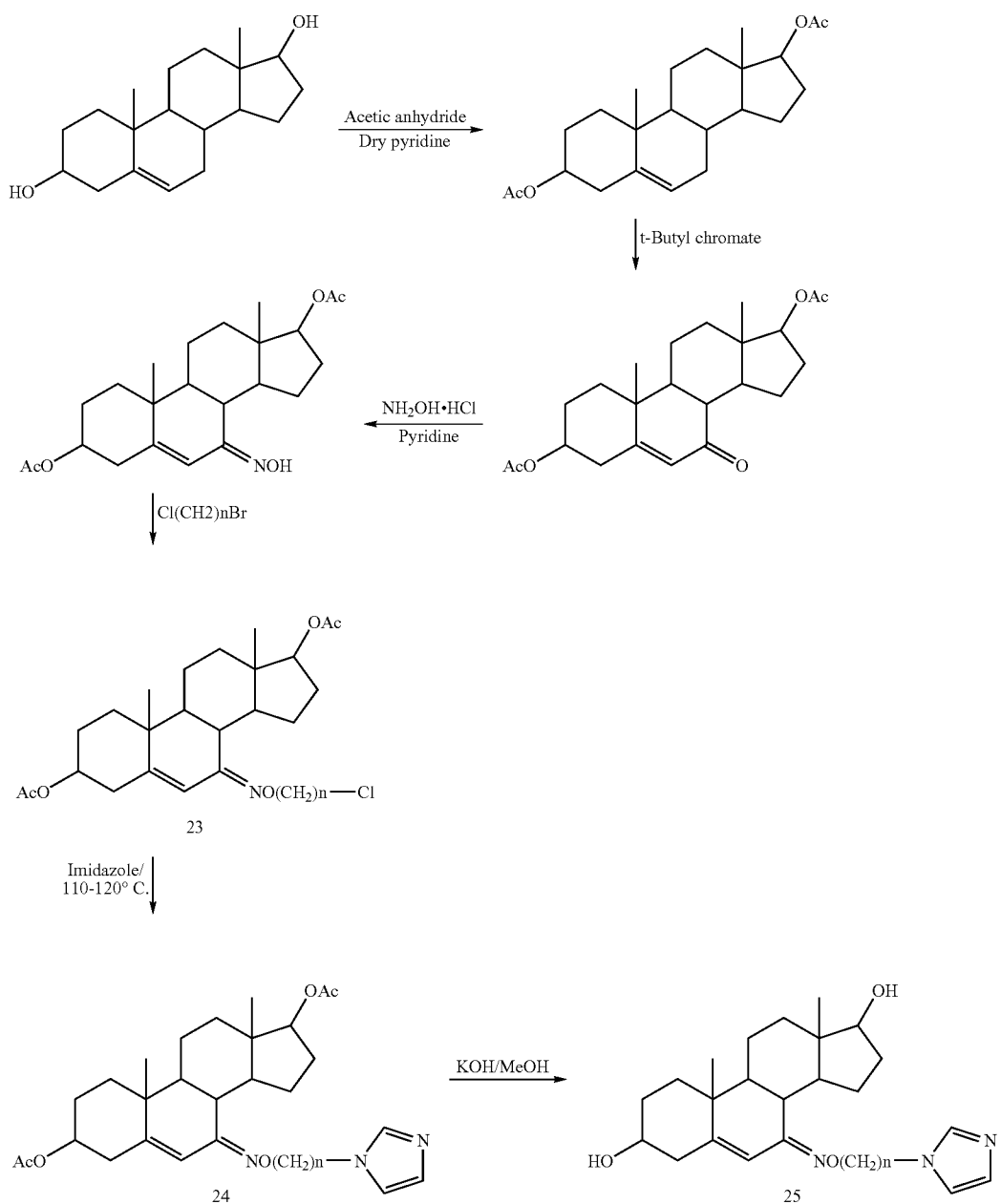
Scheme 4

Scheme 5

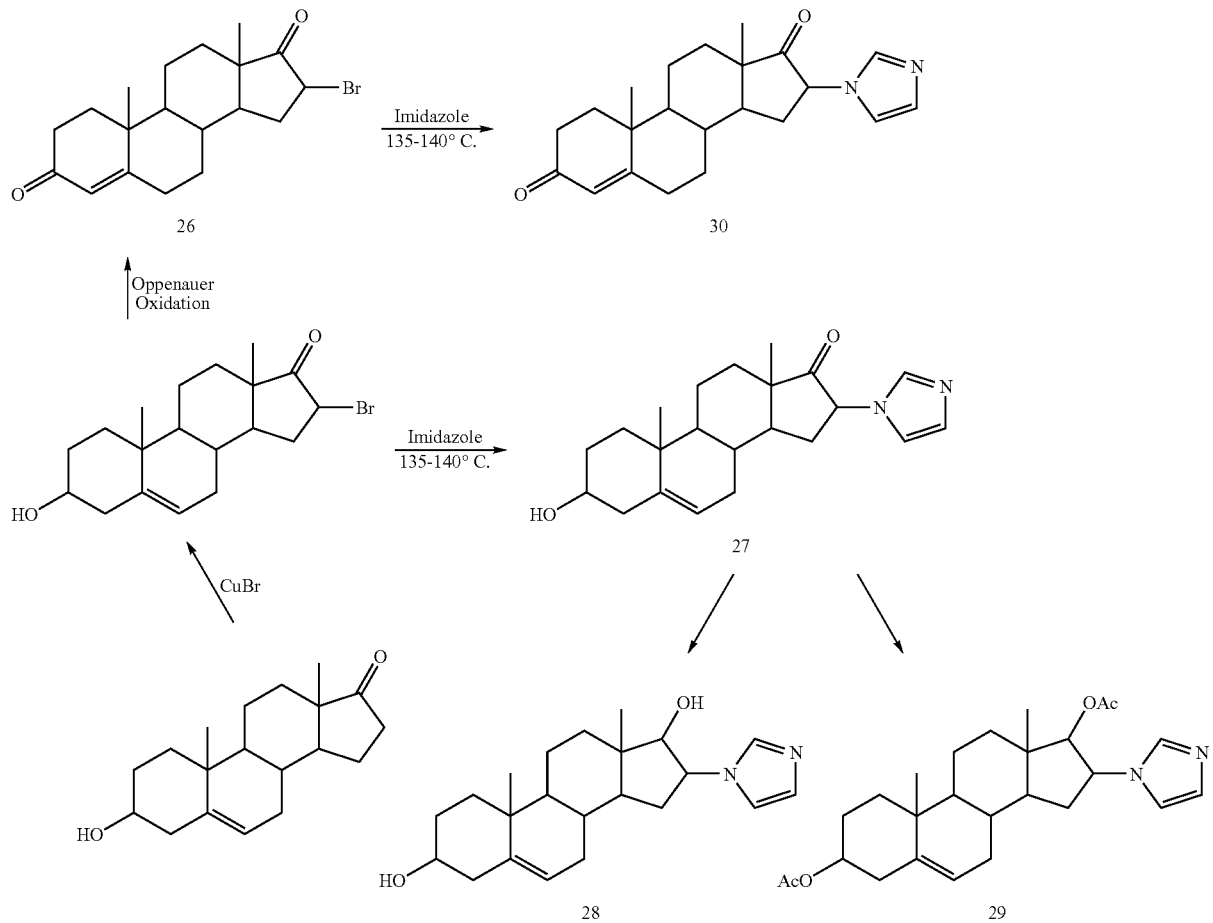

Biological Activity

The enzyme was obtained from the microsomal fraction of freshly delivered human term placental tissue according to the procedure described in literature [Thompson, E. A.; Siiteri, P. K. J.; Biol. Chem., 1974, 249, 5364-5372]. The isolated microsomes were suspended in the minimum volume of phosphate buffer (0.05M, Ph 7.4) and stored at −30° C. as described. No loss of activity was observed within 4 months.

Inhibition of Aromatase. This assay was performed similar to described methods [Foster, A. B et al, J. Med. Chem. 1983, 26, 50-54; Graves, P. E et al Endocrinology 1979, 105, 52-57] monitoring enzyme activity by measuring the 3H2O formed from [1β,2β-3H] testosterone during aromatization. Each incubation tube contained 0.225 µCi of [1β,2β-3H] testosterone, 5 µM unlabeled testosterone, 2 Mm NADPH, 20 Mm glucose-6-phosphate, 1 EU glucose-6-phosphate dehydrogenase, and inhibitor (0-250 µM) in phosphate buffer (0.05M, Ph 7.4). The test compounds had been dissolved in EtOH and diluted with buffer. The final EtOH concentration of control and inhibitor incubation was 2%. Each tube was preincubated for 5 min at 30° C. in a shaking water bath. Microsomal protein (0.5 mg) was added to start the reaction. The total volume for each incubation was 0.5 Ml. The reaction was terminated by withdrawing 100-µL aliquots at 0, 7, 14 and 21 min and pipetting them into 200 µL of a cold 1 Mm HgCl2 solution. After addition of 200 µL of an aqueous dextran-coated charcoal (DCC) suspension (2%), the vials were shaken for 20 min and centrifuged at 1500 g for 5 min to separate the charcoal-adsorbed steroids. Aliquots of the supernatant were assayed for $3H_2O$ by counting in a scintillation mixture in a Beckman liquid scintillation spectrometer (LS 8000).

TABLE 1

Aromatase inhibitory activity ($IC_{50}$) of some valuable compounds

| Compound No. | Code | Structure | Inhibition on CYP19a |
|---|---|---|---|
| 2 | DPJ-RG-1088 | 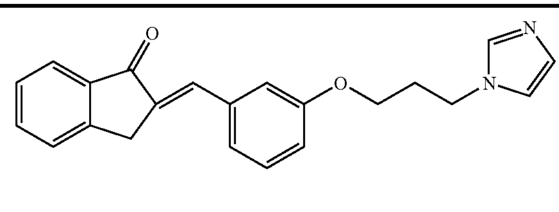 | $IC_{50}$: 0.7 Mm<br>RP: 42.5 |

TABLE 1-continued
Aromatase inhibitory activity (IC$_{50}$) of some valuable compounds
| Compound No. | Code | Structure | Inhibition on CYP19a |
|---|---|---|---|
| 4 | DPJ-RG-1055 | 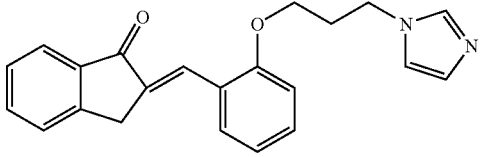 [SMILES: O=C1/C(=C/c2ccccc2OCCCn2ccnc2)Cc2ccccc21] | IC$_{50}$: 1.1 Mm<br>RP: 26.6 |
| 6 | DPJ-RG-1090 | 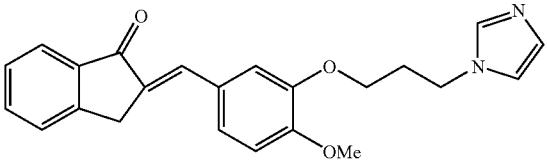 [SMILES: COc1ccc(/C=C2\Cc3ccccc3C2=O)cc1OCCCn1ccnc1] | IC$_{50}$: 1.3 Mm<br>RP: 22.5 |
| 8 | RG-DPJ-195 | 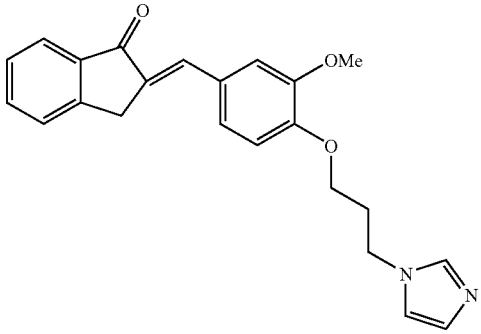 [SMILES: COc1cc(/C=C2\Cc3ccccc3C2=O)ccc1OCCCn1ccnc1] | IC$_{50}$: 0.55 Mm<br>RP: 54.1 |
| 14 | DPJ-RG-1219 | 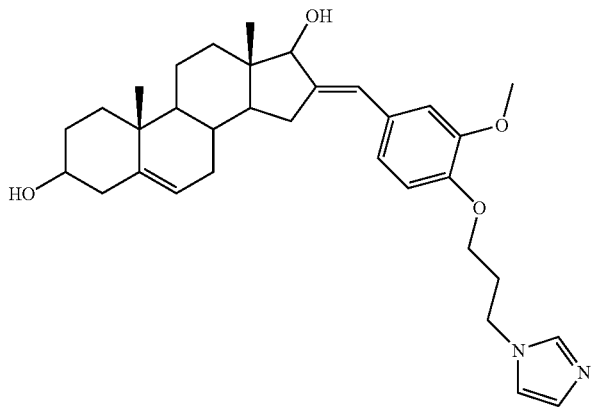 [SMILES: COc1cc(/C=C2\CC3C4CC=C5CC(O)CC[C@]5(C)C4CC[C@]3(C)C2O)ccc1OCCCn1ccnc1] | IC$_{50}$: 2.4 Mm<br>RP: 12.4 |
| 16 | DPJ-RG-1177 | 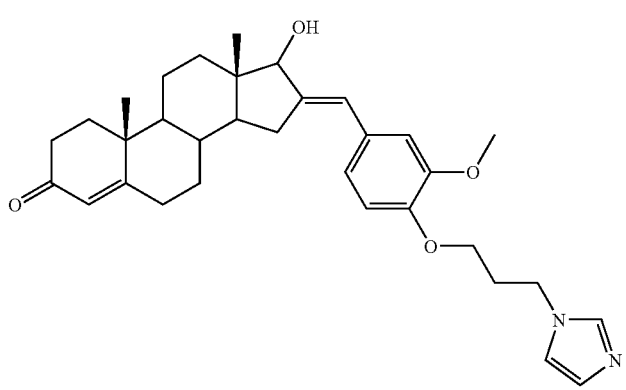 [SMILES: COc1cc(/C=C2\CC3C4CCC5=CC(=O)CC[C@]5(C)C4CC[C@]3(C)C2O)ccc1OCCCn1ccnc1] | IC$_{50}$: 4.4 μM<br>RP: 6.8 |

TABLE 1-continued

Aromatase inhibitory activity (IC$_{50}$) of some valuable compounds

| Compound No. | Code | Structure | Inhibition on CYP19a |
|---|---|---|---|
| 20 | DPJ-RG-1310 | 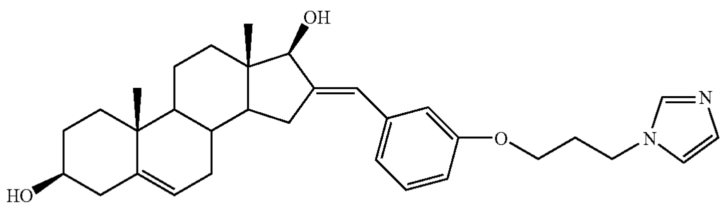 [SMILES: C[C@]12CC[C@H](O)CC1=CCC1C2CC[C@@]2(C)C1C/C(=C\c1cccc(OCCCn3ccnc3)c1)[C@@H]2O] | IC$_{50}$: 9.1 µM<br>RP: 3.3 |
| 22 | DPJ-RG-1308 | 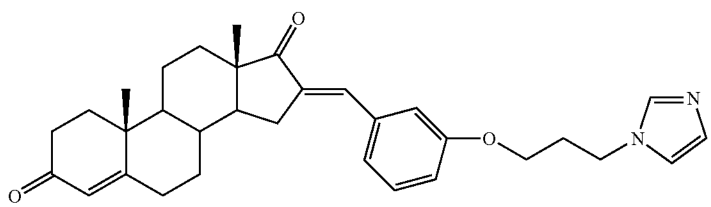 [SMILES: C[C@]12CCC(=O)C=C1CCC1C2CC[C@]2(C)C(=O)/C(=C/c3cccc(OCCCn4ccnc4)c3)CC12] | IC$_{50}$: 4.4 µM<br>RP: 6.8 |
| 24 | DPJ-RG-1315 | 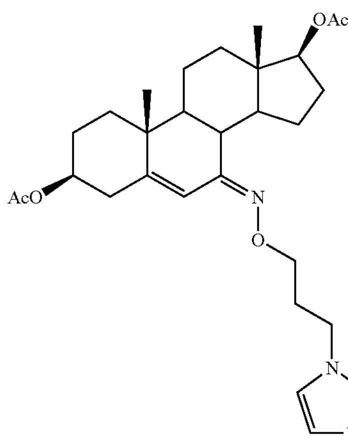 | IC$_{50}$: 3.1 µM<br>RP: 9.6 |
| 25 | DPJ-RG-1223 | 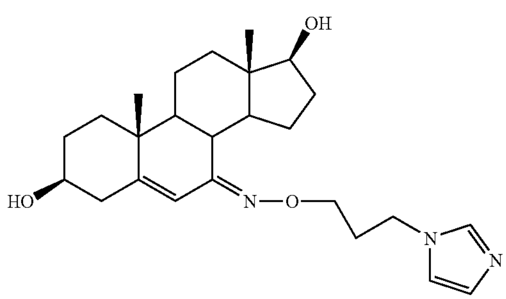 [SMILES: C[C@]12CC[C@H](O)CC1=C/C(=N/OCCCn1ccnc1)C1C2CC[C@@]2(C)C1CC[C@@H]2O] | IC$_{50}$: 12 µM<br>RP: 2.5 |
| 27 | DPJ-RG-1240 | 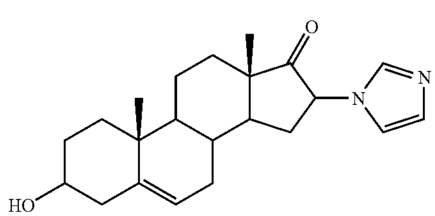 [SMILES: C[C@]12CCC(O)CC1=CCC1C2CC[C@]2(C)C(=O)C(n3ccnc3)CC12] | IC$_{50}$: 3.3 Mm<br>RP: 9.0 |

TABLE 1-continued

Aromatase inhibitory activity (IC$_{50}$) of some valuable compounds

| Compound No. | Code | Structure | Inhibition on CYP19a |
|---|---|---|---|
| | DPJ-RG-1241 | | IC$_{50}$: 0.18 Mm<br>RP: 165.3 | a) Substrate: 1β 3H-androstenedione/androstenedione 500 nm
RP: Relative potency; relative to aminoglutethimide (=1).

TABLE 2

| Compound No. | Code number | Melting point (° C.) | % Yield | Example (Method) |
|---|---|---|---|---|
| 2 | DPJ-RG-1088 | 48-50 | 46.59 | 1 |
| 4 | DPJ-RG-1055 | 76-78 | 60.3 | 1 |
| 6 | DPJ-RG-1090 | 176-180 | 55.49 | 1 |
| 8 | RG-DPJ-195 | 123-127 | 34.28 | 1 |
| 10 | RG-DPJ-325 | 218-220 | 32.24 | 1 |
| 12 | DPJ-RG-1151 | 199-201 | 71.47 | 2 |
| 13 | DPJ-RG-1196 | 109-111 | 50.04 | 2 |
| 14 | DPJ-RG-1219 | 197-198 | 84.68 | 2 |
| 15 | DPJ-RG-1227 | 163-168 | 65.64 | 2 |
| 16 | DPJ-RG-1177 | 107-109 | 75.28 | 2 |
| 18 | DPJ-RG-1307 | 211-212 | 45.87 | 2 |
| 19 | DPJ-RG-1309 | 148-150 | 47.16 | 2 |
| 20 | DPJ-RG-1310 | 133-135 | 50.20 | 2 |
| 21 | DPJ-RG-1311 | 97-99 | 34.38 | 2 |
| 22 | DPJ-RG-1308 | 81-83 | 50.25 | 2 |
| 24 | DPJ-RG-1315 | 180-182 | 32.52 | 3 |
| 25 | DPJ-RG-1223 | 205-206 | 23.45 | 3 |
| 27 | DPJ-RG-1240 | 249-251 | 51.89 | 4 |
| 28 | DPJ-RG-1317 | 285-287 | 74.57 | 4 |
| 29 | DPJ-RG-1318 | 197-199 | 64.72 | 4 |
| 30 | DPJ-RG-1241 | 179-181 | 41.45 | 4 |

We claim:

1. The imidazolyl 16-substituted-androst-4-ene-3,17-dione of the general formula A:

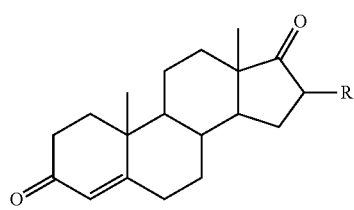

2. The imidazolyl 7-substituted-androst-5-ene steroidal derivatives of the general formula:

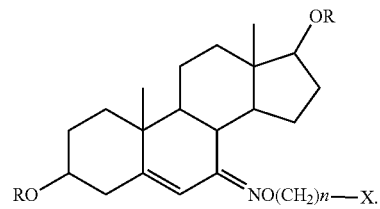

-continued

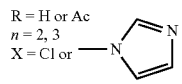
R = H or Ac
n = 2, 3
X = Cl or

3. The imidazolyl 16-substituted steroidal derivative selected from the group consisting of:

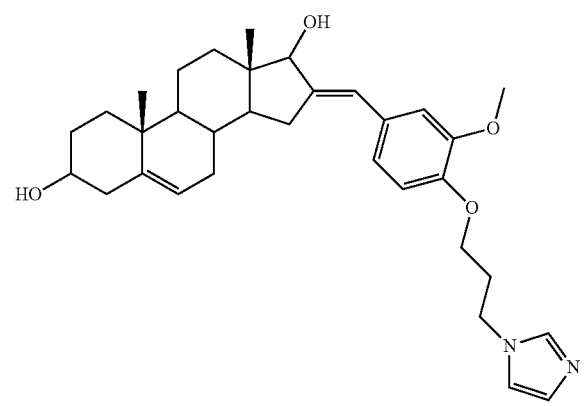

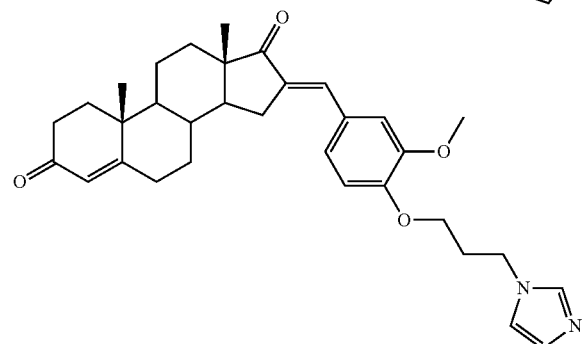

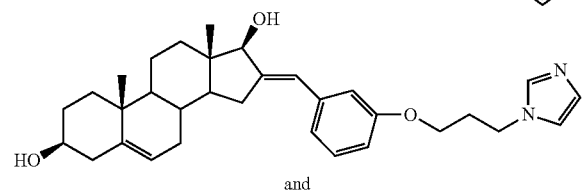

and

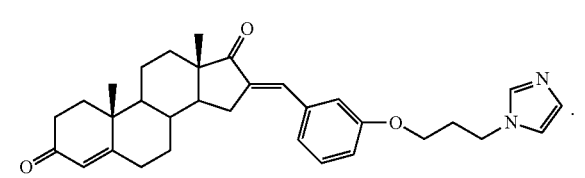

.

4. The imidazolyl substituted steroidal derivative selected from the group consisting of:

16-[4-{3-(-Imidazol-1-yl)propoxy}-3-methoxybenzylidene]-17-oxo-5-androst-en-3β-ol (12) (DPJ-RG-1151);

16-[4-{3-(Imidazol-1-yl)propoxy}-3-methoxybenzylidene]-17-oxo-5-androsten-3β-yl acetate (13) (DPJ-RG-1196);

16-[4-{3-(Imidazol-1-yl)propoxy}-3-methoxybenzylidene]-5-androstene-3β,17β-diol (14) (DPJ-RG-1219);

16-[4-{3-(Imidazol-1-yl)propoxy}-3-methoxybenzylidene]-5-androstene-3β,17β-diol diacetate (15) (DPJ-RG-1227);

16-[4-{3-(Imidazol-1-yl)propoxy}-3-methoxybenzylidene]-4-androstene-3,17-dione (16) (DPJ-RG-1177);

16-[3-{3-(Imidazol-1-yl)propoxy}benzylidene]-17-oxo-5-androstene-3β-ol (18) (DPJ-RG-1307);

16-[3-{3-(Imidazol-1-yl)propoxy}benzylidene]-17-oxo-5-androstene-3β-yl acetate (19) (DPJ-RG -1309);

16-[3-{3-(Imidazoi-1-yl)propoxy}benzylidene]-5-androstene-3β,17β-diol (20) (DPJ-RG-1310);

16-[3-{3-(Imidazol-1-yl)propoxy}benzylidene]-5-androstene-3β,17β-diol diacetate (21) (DPJ-RG-1311);

16-[3-{3-(Imidazol-1-yl)propoxy}benzylidene]-4-androstene-3,17-dione (22) (DPJ-RG-1308);

7-[O-{3-(Imidazol-1-yl)propyl}oximino]-5-androstene-3β,17β-diol diacetate (24) (DPJ-RG-1315);

7-[O-{3-(Imidazol-1-yl)propyl}oximino]-5-androstene-3β,17β-diol (25) (DPJ-RG-1223);

16β-(Imidazol-1-yl)-17-oxo-5-androsten-3β-ol (27) (DPJ-RG-1240);

16β-(Imidazol-1-yl)-5-and rostene-3β,17β-diol (28) (DPJ-RG-1317);

16β-(Imidazol-1-yl)-5-androstene-3β,17β-diol diacetate (29) (DPJ-RG-1318); and

16β-(Imidazol-1-yl)-4-androstene-3,17-dione (30) (DPJ-RG-1241).

5. The imidazolyl substituted steroidal derivative as claimed in any of claims 1-4 wherein the $IC_{50}$ value for the aromatase inhibitory activity of the compound is ranging between 0.18-12 μM with relative potency of the compound ranging from 2.5 to 165.3 times as compared to standard drug aminoglutethimide.

6. A pharmaceutical composition comprising an effective amount of the imidazolyl substituted steroidal derivative as claimed in any of claims 1-4 or a salt thereof, and a pharmaceutically acceptable carrier, adjuvant, excipient, and/or diluent.

* * * * *

UNITED STATES PATENT AND TRADEMARK OFFICE
CERTIFICATE OF CORRECTION

PATENT NO. : 8,361,996 B2  Page 1 of 1
APPLICATION NO. : 11/992141
DATED : January 29, 2013
INVENTOR(S) : Bansal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1181 days.

Signed and Sealed this
First Day of September, 2015

Michelle K. Lee
*Director of the United States Patent and Trademark Office*